(12) United States Patent
Dunman et al.

(10) Patent No.: US 9,693,999 B2
(45) Date of Patent: *Jul. 4, 2017

(54) SMALL MOLECULE RNASE INHIBITORS AND METHODS OF USE

(71) Applicants: UNIVERSITY OF ROCHESTER, Rochester, NY (US); BOARD OF REGENTS OF THE UNIVERSITY OF NEBRASKA, Lincoln, NE (US); TEMPLE UNIVERSITY—OF THE COMMONWEALTH SYSTEM OF HIGHER EDUCATION, Philadelphia, PA (US)

(72) Inventors: Paul M. Dunman, Pittsford, NY (US); Patrick D. Olson, St. Louis, MO (US); Wayne Childers, New Hope, PA (US)

(73) Assignees: University of Rochester, Rochester, NY (US); Board of Regents of the University of Nebraska, Lincoln, NE (US); Temple University—Of the Commonwealth System of Higher Education, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/933,804

(22) Filed: Nov. 5, 2015

(65) Prior Publication Data

US 2016/0115124 A1 Apr. 28, 2016

Related U.S. Application Data

(63) Continuation of application No. 13/981,015, filed as application No. PCT/US2012/022662 on Jan. 26, 2012, now Pat. No. 9,233,095.

(60) Provisional application No. 61/436,342, filed on Jan. 26, 2011.

(51) Int. Cl.

| | | |
|---|---|---|
| *A61K 31/402* | (2006.01) | |
| *C07D 207/337* | (2006.01) | |
| *A61K 31/427* | (2006.01) | |
| *C07D 307/68* | (2006.01) | |
| *C07D 307/56* | (2006.01) | |
| *C07D 405/06* | (2006.01) | |
| *C07D 417/06* | (2006.01) | |
| *A61K 31/341* | (2006.01) | |
| *A61K 45/06* | (2006.01) | |
| *C12Q 1/44* | (2006.01) | |

(52) U.S. Cl.
CPC .......... *A61K 31/427* (2013.01); *A61K 31/341* (2013.01); *A61K 31/402* (2013.01); *A61K 45/06* (2013.01); *C07D 207/337* (2013.01); *C07D 307/56* (2013.01); *C07D 307/68* (2013.01); *C07D 405/06* (2013.01); *C07D 417/06* (2013.01); *C12Q 1/44* (2013.01); *G01N 2333/922* (2013.01); *G01N 2500/04* (2013.01); *G01N 2500/10* (2013.01)

(58) Field of Classification Search
CPC .......................... A61K 31/402; C07D 207/337
See application file for complete search history.

(56) References Cited

U.S. PATENT DOCUMENTS

| | | |
|---|---|---|
| 6,936,432 B2 | 8/2005 | Gopalan et al. |
| 2002/0123077 A1 | 9/2002 | O'Toole et al. |
| 2003/0134904 A1 | 7/2003 | Giordano et al. |
| 2004/0176277 A1 | 9/2004 | Sowadski et al. |
| 2004/0180889 A1 | 9/2004 | Suto et al. |
| 2005/0042674 A9 | 2/2005 | Yu et al. |
| 2005/0187409 A1 | 8/2005 | Powers et al. |
| 2008/0090825 A1 | 4/2008 | Chikauchi et al. |
| 2009/0163545 A1 | 6/2009 | Goldfarb |

FOREIGN PATENT DOCUMENTS

| | | |
|---|---|---|
| DE | 264918 A1 | 2/1989 |
| JP | 03182742 A | 8/1991 |
| WO | 2010003533 A2 | 1/2010 |
| WO | 2012103336 A1 | 8/2012 |

OTHER PUBLICATIONS

Klumpp et al. (Current Pharmaceutical Design, 2006, 12, 1909-1922).*
Sahner et al. (European Journal of Medicinal Chemistry, 65 (2013), p. 223-231).*
Kubinyi (3D QSAR in Drug Design: Ligand-Protein Interactions and Molecular Similarity, vol. 2-3, Springer, 1998, 800 pages). pp. 243-244 provided.*
Wermuth, The Practice of Medicinal Chemsitry, 2d ed. (2003), 768 pages. Chs. 9-10 provided.*
PubChem CID 1268985, retrieved from the Internet: <URL: http://pubchem.ncbi.nlm.nih.gov/summary/summary.cgi?cid=1268985&loc=ec_rcs. Retrieved Apr. 16, 2012, Jul. 10, 2005.
PubChem C ID 5031694, retrieved from the Internet: <URL: http://pubchem.ncbi.nlm.nih.gov/summary/summary.cgi?cid=5031694> [retrieved Jun. 23 2012] Sep. 18, 2005.
Database Registry, Chemical abstracts service, Columbus, Ohio, US, XP002724925, Database accession No. 940113-01-9 the whole document, Jun. 29, 2007.
Database Registry, Chemical abstracts service, Columbus, Ohio, US, XP002724926, Database accession No. 940112-35-6 the whole document, Jun. 29, 2007.
U.S. Appl. No. 13/981,011, "Notice of Allowance", Mar. 20, 2015, 30 pages.

(Continued)

*Primary Examiner* — Robert Havlin
(74) *Attorney, Agent, or Firm* — Kilpatrick Townsend & Stockton, LLP

(57) ABSTRACT

Small molecule inhibitors of bacterial ribonuclease (e.g., RnpA) and methods for their synthesis and use are described herein. The methods of using the compounds include treating and preventing microbial infections and inhibiting bacterial ribonuclease. Also described herein are methods of identifying compounds for treating or preventing a microbial infection.

7 Claims, 6 Drawing Sheets

(56) References Cited

OTHER PUBLICATIONS

U.S. Appl. No. 13/981,015, "Advisory Action", Jul. 30, 2015, 3 pages.
U.S. Appl. No. 13/981,015, "Advisory Action", May 18, 2015, 3 Pages.
U.S. Appl. No. 13/981,015, "Final Office Action", Feb. 3, 2015, 8 pages.
U.S. Appl. No. 13/981,015, "Non final office action", Oct. 16, 2014, 14 Pages.
U.S. Appl. No. 13/981,015, "Notice of Allowance", Oct. 8, 2015, 7 pages.
Akaike, T. "A new look at the statistical model identification", IEEE Transactions on Automatic Control, vol. 19, No. 6, Dec. 1974, pp. 716-723.
Altschul et al., "Basic local alignment search tool", J Mol Biol., vol. 215, No. 3, 1990, pp. 403-410.
Anderson et al., "Characterization of the *Staphylococcus aureus* heat-shock, cold-shock, stringent, and SOS responses and their effects on log-phase mRNA turnover", J. Bacteriology, vol. 188, 2006, pp. 6739-6756.
Anderson et al., "Messenger RNA Turnover Processes in *Escherichia coli*, *Bacillus subtilis*, and Emerging Studies in *Staphylococcus aureus*", International Journal of Microbiology, Article ID 525491, 2009, pp. 1-15.
Appelbaum, "Reduced glycopeptide susceptibility in methicillin-resistant *Staphylococcus aureus* (MRSA)", International Journal of Antimicrobial Agents, vol. 30, No. 5, 2007, pp. 398-408.
Arraiano et al., "The critical role of RNA processing and degradation in the control of gene expression", FEMS Microbiology Reviews, vol. 34, 2010, pp. 883-923.
AU2012211299, "Patent Examination Report No. 1", Mar. 16, 2016, 5 pages.
Bae et al., "*Staphylococcus aureus* virulence genes identified by bursa aurealis mutagenesis and nematode killing", Proceedings of the National Academy of Sciences, vol. 101, No. 33, Aug. 10, 2004, pp. 12317-12317.
Bancroft et al., "Antimicrobial Resistance: It's Not Just for Hospitals", Jama, vol. 298, 2007, pp. 1803-1804.
Beenken et al., "Global Gene Expression in *Staphylococcus aureus* Biofilms", Journal of Bacteriology, vol. 186, 2004, pp. 4665-4684.
Carpousis, AJ, "The RNA Degradosome of *Escherichia coli*: An mRNA-Degrading Machine Assembled on RNase E", Annual Review of Microbiology, vol. 61, 2007, pp. 71-87.
Charpentier et al., "Novel cassette-based shuttle vector system for gram-positive bacteria", Applied and Environmental Microbiology, vol. 70, 2004, pp. 6076-6085.
Chaudhuri et al., "Comprehensive identification of essential *Staphylococcus aureus* genes using Transposon-Mediated Differential Hybridisation", BMC Genomics, vol. 10, No. 291, 2009, 18 pages.
Cherbuliez et al., "Etude de structures peptidiques a l'aide de phenylisothiocyanate VI.", Sur la recation de quelques acides amines et de quelques thiols avec le phenylisothiocyanate, Helv. Chem. Acta 47, 1964, pp. 1666-1672.
Cierny, G., "Surgical treatment of osteomyelitis", Plastic Reconstructive Surgery, vol. 127, Suppl 1, 2011, pp. 190S-204S.
CN201280015124.6, "Office Action", Sep. 26, 2014, 6 Pages.
CN201280015222.X, "Office Action", Sep. 26, 2014, 7 Pages.
Commichau et al., "Novel activities of glycolytic enzymes in *Bacillus subtilis*: interactions with essential proteins involved in mRNA processing", Molecular & Cellular Proteomics, vol. 8, 2009, pp. 1350-1360.
Condon, C., "RNA processing and degradation in *Bacillus subtilis* ", Microbiology and Molecular Biology Reviews, vol. 67, 2003, pp. 157-174.
Dunman et al., "Uses of *Staphylococcus aureus* GeneChips in genotyping and genetic composition analysis", Journal of Clinical Microbiology, vol. 42, No. 9, 2004, pp. 4275-4283.
EP12738820.5, "Extended European Search Report Received", Jul. 11, 2014, 12 pages.
EP12738820.5, "Office Action", Sep. 18, 2015, 18 pages.
EP12739832.9, "Extended European Search Report", Jun. 26, 2014, 12 pages.
Esnault et al., "Pin1 modulates the type 1 immune response", PLoS One 2(2), e226, Feb. 21, 2007.
Even et al., "Ribonucleases J1 and J2: two novel endoribonucleases in *B. subtilis* with functional homology to *E. coli* RNase E.", Nucleic Acids Research, vol. 33, 2005, pp. 2141-2152.
Frank et al., "Ribonuclease P: unity and diversity in a tRNA processing ribozyme", Annual Review of Biochemistry, vol. 67, 1998, pp. 153-180.
Gossringer et al., "Analysis of RNase P protein (rnpA) expression in *Bacillus subtilis* utilizing strains with suppressible rnpA expression", Journal of Bacteriology, vol. 188, 2006, pp. 6816-6823.
Guerrier-Takada et al., "The RNA moiety of ribonuclease P is the catalytic subunit of the enzyme", Cell, vol. 35, No. 3, P2, Dec. 1983, pp. 849-857.
Hartmann, Roland et al., "The making of tRNAs and more—RNase P and tRNase Z", Progress in Molecular Biology and Translational Science, vol. 85, 2009, pp. 319-368.
He et al., "Scaling up of continuous-flow, microwave-assisted, organic reactions by varying the size of Pd-functionalized catalytic monoliths", Beilstein Journal of Organic Chemistry, vol. 7, 2011, pp. 1150-1157.
Hidalgo et al., "Characterization of the human colon carcinoma cell line (Caco-2) as a model system for intestinal epithelial permeability", Gastroenterology, vol. 96, No. 3, 1989, pp. 736-749.
Huntzinger et al., "*Staphylococcus aureus* RNAIII and The Endoribonuclease III Coordinately Regulate Spa Gene Expression", The EMBO Journal, vol. 24, No. 4, Jan. 2005, pp. 824-835.
Jendralla et al., "Synthesis and biological activity of new HMG-CoA reductase inhibitors. 2. Derivatives of 7-(1H-pyrrol-3-yl)-substituted-3,5-dihydroxyhept-6(E)-enoic (-heptanoic) acids", Journal of Medicinal Chemistry , vol. 33, No. 1, 1990, pp. 61-70.
Ji et al., "Identification of critical staphylococcal genes using conditional phenotypes generated by antisense RNA", Science, vol. 293, 2001, pp. 2266-2269.
Jiang et al., "Regions of RNase E important for 5'-end-dependent RNA cleavage and autoregulated synthesis", Journal of Bacteriology, vol. 182, No. 9, 2000, pp. 2468-2475.
Kansy et al., "Physicochemical high throughput screening: parallel artificial membrane permeation assay in the description of passive absorption processes", The Journal of Medicinal Chemistry, vol. 41, 1998, pp. 1007-1010.
Kazantsev et al., "Bacterial RNase P: A New View of an Ancient Enzyme", Nature Reviews Microbiology, vol. 4, Oct. 2006, pp. 729-740.
Khan et al., "Condensed benzopyrans. IV. Synthesis of some derivatives of 7H- and 9H-pyrano[3,2-E]indoles", Journal of Heterocyclic Chemistry, vol. 16, No. 5, 1979, pp. 997-999.
Klevens et al., "Invasive methicillin-resistant *Staphylococcus aureus* infections in the United States", Jama, vol. 298, 2007, pp. 1763-1771.
Kobayashi et al., "Essential *Bacillus subtilis* genes", Proceedings of the National Academy of Sciences, USA, vol. 100, 2003, pp. 4678-4683.
Kochansky et al., "Impact of pH on plasma protein binding in equilibrium dialysis", Molecular Pharmaceutics, vol. 5, 2008, pp. 438-448.
Kole et al., "*E. coli* RNAase P has a required RNA component", Cell, vol. 99, No. 4, 1980, pp. 881-887.
Lehnik-Habrink et al.,"The RNA degradosome in *Bacillus subtilis*: identification of CshA as the major RNA helicase in the multiprotein complex", Molecular Microbiology, vol. 77, No. 4, 2010, pp. 958-971.
Letunic et al., "SMART 5: domains in the context of genomes and networks", Nucleic Acids Research, vol. 34, 2006, pp. D257-D260.
Lew et al., "Osteomyelities", Lancet, vol. 364, 2004, pp. 369-379.
Lewis, K., "Multidrug Tolerance of Biofilms and Persister Cells", Current Topics in Microbiology and Immunology, vol. 322, 2008, pp. 107-131.

(56) References Cited

OTHER PUBLICATIONS

Li et al., "Synthesis of 1-Aryloxyacetyl-4-(5-(4-Chlorophenyl)-2-Furoyl) Semicarbazides", Synthetic Communications, vol. 31, No. 9, XP55119858, ISSN: 0039-7911, DOI: 10.1081/SCC-100104053, Jan. 1, 2001, pp. 1433-1440.
Li et al., "Synthesis of 2-(5-(2-chlorophenyl)2-furoylamido)-5-aryloxymethyl-1,3,4-thiadiazoles under microwave irradiation", Synthetic Communications, 31, 2001, pp. 1829-1836.
Liu et al., "Differential evolution of substrates for an RNA enzyme in the presence and absence of its protein cofactor", Cell, vol. 77, 1994, pp. 1093-110.
Lundblad et al., "Rapid selection of accessible and cleavable sites in RNA by *Escherichia coli* RNase P and random external guide sequences", Proc. Natl. Acad. Sci. USA, vol. 105, No. 7, Feb. 19, 2008, pp. 2354-2357.
Mackie, "Ribonuclease E is a 5'-end-dependent endonuclease", Letters to Nature, vol. 395, Oct. 15, 1998, pp. 720-724.
Mäder et al., "mRNA processing by RNases J1 and J2 affects *Bacillus subtilis* gene expression on a global scale", Mol. Microbiol, vol. 70, No. 1, Oct. 2008, pp. 183-196.
Manetti et al., "Ligand-Based Virtual Screening, Parallel Solution-Phase and Microwave-Assisted Synthesis as Tools to Identify and Synthesize New Inhibitors of Mycobacterium tuberculosis", ChemMedChem., vol. 1, No. 9, 2006, pp. 973-989.
Marvin et al., "Broadening the mission of an RNA enzyme", Journal of Cellular Biochemistry, vol. 108, No. 6, Dec. 2009, pp. 1244-1251.
Mathy et al., "5'-to-3' exoribonuclease activity in bacteria: role of RNase J1 in rRNA maturation and 5' stability of mRNA", Cell, vol. 129, No. 4, 2007, pp. 681-692.
McDougal et al., "Pulsed-field gel electrophoresis typing of oxacillin-resistant *Staphylococcus aureus* isolates from the United States: establishing a national database", Journal of Clinical Microbiology, vol. 41, No. 11, Nov. 2003, pp. 5113-5120.
McMasters et al., "Inhibition of recombinant cytochrome P450 isoforms 2D6 and 2C9 by diverse drug-like molecules", J. Med. Chem., vol. 50, No. 14, 2007, pp. 3205-3213.
Miczak et al., "Proteins Associated with RNase E in a Multicomponent Ribonucleolytic Complex", Proceedings of the National Academy of Sciences, vol. 93, No. 9, Apr. 1996, pp. 3865-3869.
Mosmann, "Rapid colorimetric assay for cellular growth and survival: application to proliferation and cytotoxicity assays", J Immunol Methods 65, Dec. 1983, pp. 55-63.
Novick, RP, "Autoinduction and Signal Transduction in the Regulation of Staphylococcal Virulence", Molecular Microbiology, vol. 48, No. 6, Jun. 2003, pp. 1429-1449.
Olson et al., "Small Molecule Inhibitors of *Staphylococcus aureus* RnpA Alter Cellular mRNA Turnover, Exhibit Antimicrobial Activity, and Attenuate Pathogenesis", PLoS Pathogens, vol. 7, No. 2, Feb. 10, 2011, pp. e1001287-1.
PCT/US2012/022662, "International Preliminary Report on Patentability", Jul. 30, 2013, 9 pages.
PCT/US2012/022662, "International Search Report", Jul. 17, 2012, 4 pages.
PCT/US2012/022724, "International Preliminary Report on Patentability", Jul. 30, 2013, 10 pages.
PCT/US2012/022724, "International Search Report and Written Opinion", Jul. 6, 2012, 4 pages.
Rao et al., "Treating osteomyelitis: antibiotics and surgery", Plast. Reconstr. Surg., vol. 127 Suppl 1, Jan. 2011, pp. 177S-187S.
Rauhut et al., "mRNA degradation in bacteria", FEMS Microbiol. Rev., vol. 23, No. 3, Jun. 1999, pp. 353-370.
Renneberg et al., "A mouse model for simultaneous pharmacokinetic and efficacy studies of antibiotics at sites of infection", J. Antimicrob. Chemother., vol. 22, No. 1, 1988, pp. 51-60.
Rice, "Federal funding for the study of antimicrobial resistance in nosocomial pathogens: no ESKAPE", The Journal of Infectious Diseases, vol. 197, No. 8, Apr. 15, 2008, pp. 1079-1081.
Roberts et al., "Characterizing the Effect of the *Staphylococcus aureus* Virulence Factor Regulator, SarA, on Log-Phase mRNA Half-Lives", Journal of Bacteriology, vol. 188, No. 7, Apr. 2006, pp. 2593-2603.
Roux et al., "Characterization of components of the *Staphylococcus aureus* mRNA degradosome holoenzyme-like complex", Journal of bacteriology, vol. 193, No. 19, Oct. 1, 2011, pp. 5520-5526.
Sahu et al., "Studies on thiazolidinones. Part XV. Synthesis of thiazolidinones from mono- and disubstituted thioureas and heterocyclic substituents", J. Ind. Chem., 62, 1985, pp. 71-73.
Sankawa et al., "Biosynthesis of natural products. IV. Biosynthesis of itaconitin", Degradation studies on itaconitin. Chem Pharm Bull (Tokyo) 17(10), 1969, pp. 2020-2024.
Schedl et al., "Mutants of *Escherichia coli* thermosensitive for the synthesis of transfer RNA", Proc. Natl. Acad. Sci. USA, vol. 70, No. 7, 1973, pp. 2091-2095.
Schepetkin et al., "Novel Small-Molecule Inhibitors of Anthrax Lethal Factor Identified By High-Throughput Screening", Journal of Medicinal Chemistry, vol. 49, No. 17, Aug. 1, 2006, pp. 5232-5244.
Schepetkin et al., "Novel Small-Molecule Inhibitors of Anthrax Lethal Factor Identified by High-Throughput Screening—Supporting Information", Journal of Medicinal Chemistry, vol. 49, No. 17, Aug. 2006, pp. S1-S10.
Schultz et al., "SMART, a simple modular architecture research tool: identification of signaling domains", Proc. Natl. Acad. Sci. USA, vol. 95, No. 11, May 26, 1998, pp. 5857-5864.
Selles, "Synthesis and biological evaluation of himanimide C and unnatural analogues", Org Lett. 7(4), 2005, pp. 605-608.
Shahbabian et al., "RNase Y, a novel endoribonuclease, initiates riboswitch turnover in *Bacillus subtilis*", EMBO J., vol. 28, No. 22, Nov. 18, 2009, pp. 3523-3533.
Shorr et al., "Healthcare-associated bloodstream infection: A distinct entity? Insights from a large U.S. database", Critical Care Medicine, vol. 34, No. 10, Oct. 2006, pp. 2588-2595.
Simchen et al., "Synthese von derivaten der a-ketocarbonsauren aus 2-O-funktionell substituierten trimethylsilykeyenacetalen", Libigs Ann. Chem., 1992, pp. 607-613.
Spitzfaden et al., "The Structure of Ribonuclease P Protein from *Staphylococcus aureus* Reveals a Unique Binding Site for Single-stranded RNA", Journal of Molecular Biology, vol. 295, Issue 1, Jan. 2000, pp. 105-115.
Takayama, Kathy et al., "The Role of RNA Stability During Bacterial Stress Responses and Starvation", Environmental Microbiology, vol. 2, No. 4, Aug. 2000, pp. 355-365.
Tian et al., "Studies of intestinal permeability of 36 flavonoids using Caco-2 cell monolayer model", Int. J. Pharm., vol. 367, Feb. 9, 2009, pp. 58-64.
Vanzo et al., "Ribonuclease E organizes the Protein Interactions in the *Escherichia coli* RNA Degradosome", Genes Development, vol. 12, No. 17, Sep. 1998, pp. 2770-2781.
Walker et al., "Ribonuclease P: the evolution of an ancient RNA enzyme", Crit. Rev. Biochem. Mol. Biol., vol. 41, No. 2, 2006, pp. 77-102.
Wang et al., "Expeditious One-Step Method to 5-Aryl-2-furoyl Substituted Thioureas and Thiosemicarbazides in Aqueous Media", Synthetic Communications, vol. 36, No. 7, XP55119842, ISSN: 0039-7911, DOI: 10.1080/00397910500464244, Mar. 1, 2006, pp. 843-847.
Wang et al., "Microwave induced synthesis of 2-(2-Furoylamid0)-5-Aryloxymethyl-1,3,4-Thiadiazoles", Synthetic Communications, vol. 31, No. 16, XP55119851, ISSN: 0039-7911, DOI: 10.1081/SCC-100105133, Jan. 1, 2011, pp. 2537-2541.
Waugh et al., "Complementation of an RNase P RNA (rnpB) gene deletion in *Escherichia coli* by homologous genes from distantly related eubacteria", Journal of Bacteriology, vol. 172, No. 11, Nov. 1990, pp. 6316-6322.
Weiss et al., "Impact of sarA on antibiotic susceptibility of *Staphylococcus aureus* in a catheter-associated in vitro model of biofilm formation", Antimicrob. Agents Chemother., vol. 53, No. 6, Jun. 2009, pp. 2475-2482.

(56) References Cited

OTHER PUBLICATIONS

Weiss et al., "Impact of sarA on daptomycin susceptibility of *Staphylococcus aureus* biofilms in vivo", Antimicrob Agents Chemother., vol. 53, No. 10, Oct. 2009, pp. 4096-4102.

Wohnsland et al., "High-Throughput Permeability pH Profile and High-Throughput Alkane/Water log P with Artificial Membranes", Journal of Medicinal Chemistry, vol. 44, No. 6, Mar. 2001, pp. 923-930.

Yang, Jiansong et al., "Misuse of the Well-Stirred Model of Hepatic Drug Clearance", Drug Metabolism and Disposition, vol. 35, No. 3, Apr. 2007, pp. 501-502.

Yao, S. et al., "*Bacillus subtilis* RNase J1 endonuclease and 5' exonuclease activities in the turnover of DeltaermC mRNA", RNA, vol. 15, No. 12, Dec. 2009, pp. 2331-2339.

Zetola et al., "Community-acquired meticillin-resistant *Staphylococcus aureus*: an emerging threat", Lancet Infect Dis., vol. 5 (5), May 2005, pp. 275-286.

Zhang et al., "Impact of azaproline on amide cis-trans isomerism: conformational analyses and NMR studies of model peptides including TRH analogues", J Am Chem Soc., 125(4), 2003, pp. 1221-1235.

Australian Patent Application No. 2012211299, Patent Examination Report No. 2 mailed Sep. 20, 2016, 4 pages.

\* cited by examiner

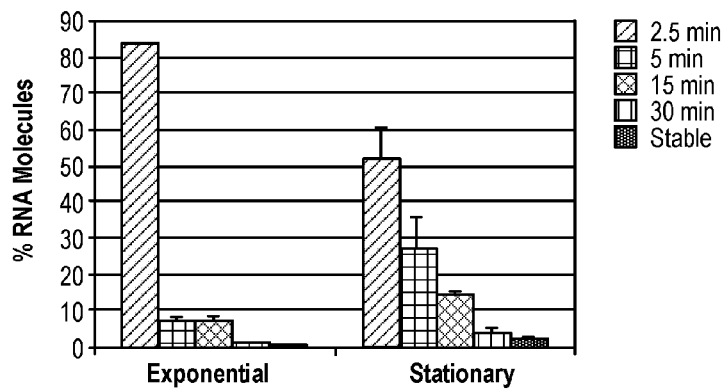
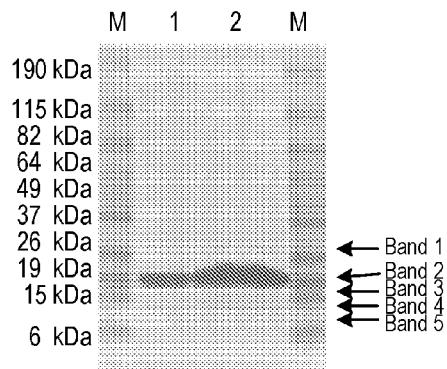
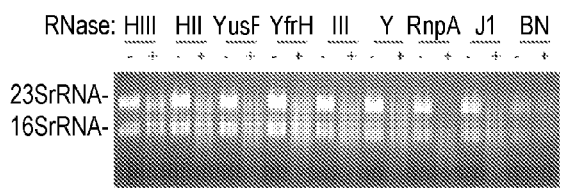
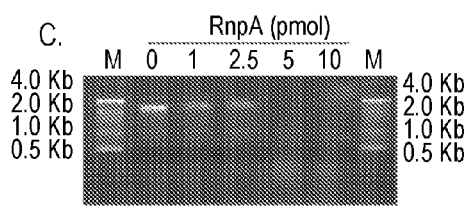
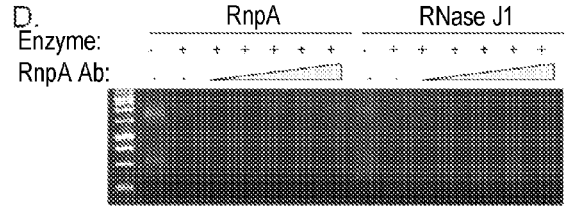
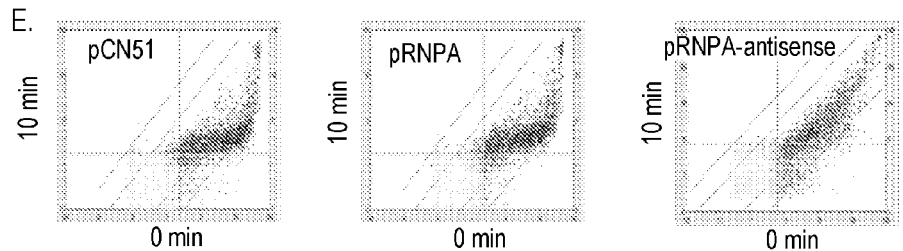
Figure 1
Figure 2

SEQUENCE LISTING

<160> NUMBER OF SEQ ID NOS: 9

<210> SEQ ID NO 1
<211> LENGTH: 115
<212> TYPE: PRT
<213> ORGANISM: S. aureus

<400> SEQUENCE: 1

Met Glu Lys Ala Tyr Arg Ile Lys Lys Asn Ala Asp Phe Gln Arg Ile
1               5                   10                  15

Tyr Lys Lys Gly His Ser Val Ala Asn Arg Gln Phe Val Val Tyr Thr
            20                  25                  30

Cys Asn Asn Lys Glu Ile Asp His Phe Arg Leu Gly Ile Ser Val Ser
        35                  40                  45

Lys Lys Leu Gly Asn Ala Val Leu Arg Asn Lys Ile Lys Arg Ala Ile
    50                  55                  60

Arg Glu Asn Phe Lys Val His Lys Ser His Ile Leu Ala Lys Asp Ile
65                  70                  75                  80

Ile Val Ile Ala Arg Gln Pro Ala Lys Asp Met Thr Thr Leu Gln Ile
                85                  90                  95

Gln Asn Ser Leu Glu His Val Leu Lys Ile Ala Lys Val Phe Asn Lys
            100                 105                 110

Lys Ile Lys
        115

<210> SEQ ID NO 2

```
<211> LENGTH: 117
<212> TYPE: PRT
<213> ORGANISM: S. epidermidis

<400> SEQUENCE: 2

Met Leu Leu Glu Lys Ala Tyr Arg Ile Lys Lys Asn Ala Asp Phe Gln
1               5                   10                  15

Arg Ile Tyr Lys Lys Gly His Ser Val Ala Asn Arg Gln Phe Val Val
            20                  25                  30

Tyr Thr Cys Asn Asn Lys Glu Ile Asp His Phe Arg Leu Gly Ile Ser
        35                  40                  45

Val Ser Lys Lys Leu Gly Asn Ala Val Leu Arg Asn Lys Ile Lys Arg
    50                  55                  60

Ala Ile Arg Glu Asn Phe Lys Val His Lys Ser His Ile Leu Ala Lys
65                  70                  75                  80

Asp Ile Ile Val Ile Ala Arg Gln Pro Ala Lys Asp Met Thr Thr Leu
                85                  90                  95

Gln Ile Gln Asn Ser Leu Glu His Val Leu Lys Ile Ala Lys Val Phe
            100                 105                 110

Asn Lys Lys Ile Lys
        115

<210> SEQ ID NO 3
<211> LENGTH: 123
<212> TYPE: PRT
<213> ORGANISM: S. pneumoniae

<400> SEQUENCE: 3

Met Lys Lys Asn Phe Arg Val Lys Arg Glu Lys Asp Phe Lys Ala Ile
1               5                   10                  15

Phe Lys Glu Gly Thr Ser Phe Ala Asn Arg Lys Phe Val Val Tyr Gln
            20                  25                  30

Leu Glu Asn Gln Lys Asn His Phe Arg Val Gly Leu Ser Val Ser Lys
        35                  40                  45

Lys Leu Gly Asn Ala Val Thr Arg Asn Gln Ile Lys Arg Arg Ile Arg
    50                  55                  60

His Ile Ile Gln Asn Ala Lys Gly Ser Leu Val Glu Asp Val Asp Phe
65                  70                  75                  80

Val Val Ile Ala Arg Lys Gly Val Glu Thr Leu Gly Tyr Ala Glu Met
                85                  90                  95

Glu Lys Asn Leu Leu His Val Leu Lys Leu Ser Lys Ile Tyr Arg Glu
            100                 105                 110

Gly Asn Gly Ser Glu Lys Glu Thr Lys Val Asp
        115                 120

<210> SEQ ID NO 4
<211> LENGTH: 119
<212> TYPE: PRT
<213> ORGANISM: S. pyogenes

<400> SEQUENCE: 4

Met Lys Lys Thr Tyr Arg Val Lys Arg Glu Lys Asp Phe Gln Ala Ile
1               5                   10                  15

Phe Lys Asp Gly Lys Ser Thr Ala Asn Arg Lys Phe Val Ile Tyr His
            20                  25                  30

Leu Asn Arg Gly Gln Asp His Phe Arg Val Gly Ile Ser Val Gly Lys
        35                  40                  45
```

-continued

```
Lys Ile Gly Asn Ala Val Thr Arg Asn Ala Val Lys Arg Lys Ile Arg
         50                  55                  60

His Val Ile Met Ala Leu Gly His Gln Leu Lys Ser Glu Asp Phe Val
 65                  70                  75                  80

Val Ile Ala Arg Lys Gly Val Glu Ser Leu Glu Tyr Gln Glu Leu Gln
                 85                  90                  95

Gln Asn Leu His His Val Leu Lys Leu Ala Gln Leu Leu Lys Gly
                100                 105                 110

Phe Glu Ser Glu Glu Lys His
            115

<210> SEQ ID NO 5
<211> LENGTH: 118
<212> TYPE: PRT
<213> ORGANISM: E. faecalis

<400> SEQUENCE: 5

Met Lys Lys Ser Tyr Arg Val Lys Lys Glu Lys Glu Phe Gln Gln Val
 1               5                  10                  15

Phe Asn Lys Gln Ser Cys Ala Asn Arg Arg Phe Val Tyr Val
             20                  25                  30

Leu Glu Lys Pro Gln Gln Ala His Phe Arg Val Gly Ile Ser Val Gly
             35                  40                  45

Lys Lys Ile Gly Asn Ala Val Thr Arg Asn Ala Val Lys Arg Lys Ile
         50                  55                  60

Arg Ala Ser Leu Phe Gln Leu Lys Asp Arg Ile Ser Pro Glu Ile Asp
 65                  70                  75                  80

Phe Ile Val Ile Ala Arg Pro Gly Leu Glu Lys Leu Ser Ser Glu Glu
                 85                  90                  95

Val Lys Ala Asn Leu Thr His Val Leu Asn Leu Ala Lys Ile Leu Asp
                100                 105                 110

Val Arg Glu Gly Ile Glu
            115

<210> SEQ ID NO 6
<211> LENGTH: 119
<212> TYPE: PRT
<213> ORGANISM: E. coli

<400> SEQUENCE: 6

Met Val Lys Leu Ala Phe Pro Arg Glu Leu Arg Leu Leu Thr Pro Ser
 1               5                  10                  15

Gln Phe Thr Phe Val Phe Gln Gln Pro Gln Arg Ala Gly Thr Pro Gln
             20                  25                  30

Ile Thr Ile Leu Gly Arg Leu Asn Ser Leu Gly His Pro Arg Ile Gly
             35                  40                  45

Leu Thr Val Ala Lys Lys Asn Val Arg Arg Ala His Glu Arg Asn Arg
         50                  55                  60

Ile Lys Arg Leu Thr Arg Glu Ser Phe Arg Leu Arg Gln His Glu Leu
 65                  70                  75                  80
```

Pro Ala Met Asp Phe Val Val Ala Lys Lys Gly Val Ala Asp Leu
            85                  90                  95

Asp Asn Arg Ala Leu Ser Glu Ala Leu Glu Lys Leu Trp Arg His
        100                 105                 110

Cys Arg Leu Ala Arg Gly Ser
        115

<210> SEQ ID NO 7
<211> LENGTH: 130
<212> TYPE: PRT
<213> ORGANISM: A. baumannii

<400> SEQUENCE: 7

Met Ala Leu Tyr Ser Phe Ser Thr Asp Leu Arg Ile Arg Cys Ala Ala
1               5                   10                  15

Asp Tyr Lys Ser Val Phe Asp Gly Ala Leu Phe Lys Val His Gln Pro
            20                  25                  30

His Phe Leu Phe Leu Ala Lys Leu Thr Glu Gln Pro Asn Ser Arg Leu
        35                  40                  45

Gly Ile Val Val Ala Lys Lys Lys Val Arg Arg Ala His Glu Arg Asn
    50                  55                  60

Arg Ile Lys Arg Leu Ala Arg Glu Ser Phe Arg Leu His Gln Pro Lys
65                  70                  75                  80

Phe Gly Ser Asp Ile Asp Val Val Met Pro Lys Val Gly Ile Glu
            85                  90                  95

Thr Ile Thr Asn Ala Glu Leu Tyr Gln Gln Leu Asp Phe Ala Trp Gln
            100                 105                 110

Lys Leu Gln Arg Leu Ala Lys Lys His Ser Lys Val Val Pro Thr Ser
        115                 120                 125

Gln Asn
    130

<210> SEQ ID NO 8
<211> LENGTH: 40
<212> TYPE: DNA
<213> ORGANISM: Artificial sequence
<220> FEATURE:
<223> OTHER INFORMATION: Synthetic construct

<400> SEQUENCE: 8
gaattctcaa ataaaaacga taaataagcg agtgatgtta                         40

<210> SEQ ID NO 9
<211> LENGTH: 38
<212> TYPE: DNA
<213> ORGANISM: Artificial sequence
<220> FEATURE:
<223> OTHER INFORMATION: Synthetic Construct

<400> SEQUENCE: 9
ggtaccttac ttaatctttt tattaaaaac tttggcaa                           38

SMALL MOLECULE RNASE INHIBITORS AND METHODS OF USE

CROSS-REFERENCE TO PRIORITY APPLICATIONS

This application is a continuation of U.S. application Ser. No. 13/981,015, filed on Jul. 22, 2013, which is a U.S. national stage application under 35 U.S.C. §371 of PCT/US2012/022662, filed on Jan. 26, 2012, which claims priority to U.S. Provisional Application No. 61/436,342, filed Jan. 26, 2011, all of which are incorporated herein by reference in their entireties.

STATEMENT REGARDING FEDERALLY FUNDED RESEARCH

This invention was made with government support under grant number AI073780 awarded by the National Institutes of Health. The government has certain rights in the invention.

FIELD

The subject matter disclosed herein generally relates to small molecule inhibitors of bacterial ribonuclease (RNase) and methods of their preparation. Also, the subject matter described herein generally relates to methods of using the small molecule inhibitors described herein to treat and prevent microbial infections.

BACKGROUND

*Staphylococcus aureus* infections are often associated with high rates of morbidity and mortality (see Shorr et al., *Crit Care Med,* 34: 2588-2595 (2006)). Indeed, reports estimate that in 2005 the organism caused more U.S. deaths than HIV/AIDS (see Bancroft, E. A., *Jama,* 298: 1803-1804 (2007); Klevens et al., *Jama,* 298: 1763-1771 (2007)). The emergence of vancomycin-resistant, methicillin-resistant, multidrug-resistant, and hypervirulent strains has further accentuated the need for novel antibiotics (see Appelbaum, P. C., *Int J Antimicrob Agents,* 30: 398-408 (2007); Zetola et al., *Lancet Infect Dis,* 5: 275-286 (2005)). Bacterial RNA processing and degradation are required cellular processes that can be exploited for antimicrobial drug discovery.

Much of the understanding of bacterial RNA degradation comes from studies of *Escherichia coli* where bulk mRNA decay is thought to be catalyzed by a holoenzyme complex (RNA degradosome), which consists of at least four subunits: RNase E (rne), RNA helicase (rhlB), enolase (eno), and PNPase (pnpA) (see Carpousis, A. J., *Annu Rev Microbiol,* 61: 71-87 (2007)). RNase E is an essential ribonuclease and a key component of the degradosome complex. It serves as a scaffold for the assembly of other members of the RNA degradosome and catalyzes the initial endoribonucleolytic event during substrate degradation (see Mackie, G. A., *Nature,* 395: 720-723 (1998); Vanzo et al., *Genes Dev,* 12: 2770-2781 (1998)). Based on its essentiality, RNase E could be considered an appropriate target for antibiotic drug discovery. However, many Gram-positive bacteria, including *S. aureus,* lack an RNase E amino acid ortholog (see Condon, C., Microbiol *Mol Biol Rev,* 67: 157-174 (2003)). As a consequence, their degradation components and mechanism(s) of mRNA decay are less understood.

Recent studies suggest that at least two ribonucleases, RNase J1 and RNase Y, contribute to bulk mRNA degradation within *Bacillus subtilis,* and presumably other Gram-positive bacteria. *B. subtilis* ribonuclease J1 is a bifunctional ribonuclease, with 5' exonuclease and endonuclease activities, that mediates mRNA degradation in vitro (see Even et al., *Nucleic Acids Res,* 33: 2141-2152 (2005); Mathy et al., *Cell,* 129: 681-692 (2007)). The enzyme has also been found to interact with enolase (a component of the *E. coli* RNA degradosome) and RNase J1 depleted *B. subtilis* strains demonstrate a moderate decrease in mRNA decay, suggesting that it may be the functional equivalent to *E. coli* RNase E (see Even et al., *Nucleic Acids Res,* 33: 2141-2152 (2005); Commichau et al., *Mol Cell Proteomics,* 8: 1350-1360 (2009); Mader et al., *Mol Microbiol,* 70: 183-196 (2008)). However, mRNA turnover still occurs in RNase J1 diminished cells and RNA species containing 5' strong-hairpin structures are not effectively degraded by the enzyme, indicating that additional factors are likely to contribute to *B. subtilis* cellular RNA degradation (see Yao et al., *Rna,* 15: 2331-2339 (2009)). Ribonuclease Y is a recently identified endonuclease that may ostensibly work in concert with RNase J1 to mediate bulk RNA decay. RNase Y can cleave mRNA molecules containing high-order secondary structures and globally affects cellular messenger RNA turnover (see Shahbabian et al., *Embo J,* 28: 3523-3533 (2009)). Both RNase J1 and RNase Y are essential enzymes and, in that regard, could be considered targets for antimicrobial drug discovery (see Kobayashi et al., *Proc Natl Acad Sci USA,* 100: 4678-4683 (2003)). However, it remains to be seen whether RNase J1, RNase Y, and/or previously uncharacterized ribonucleases modulate mRNA decay within *S. aureus.*

SUMMARY

In accordance with the purposes of the disclosed materials, compounds, compositions, kits, and methods, as embodied and broadly described herein, the disclosed subject matter relates to compositions, methods of making said compositions, and methods of using said compositions. More specifically, compounds and compositions for use as inhibitors of bacterial ribonuclease (RNase) are provided herein. A class of RNase inhibitors includes compounds of the following structure:

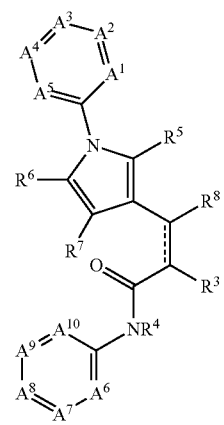

and pharmaceutically acceptable salts and prodrugs thereof. In these compounds, ===== is a single or double bond; $A^1$, $A^2$, $A^3$, $A^4$, and $A^5$, are each independently selected from N or $CR^1$; $A^6$, $A^7$, $A^8$, $A^9$, and $A^{10}$ are each independently selected from N or $CR^2$; each $R^1$, each $R^2$, $R^3$, $R^5$, $R^6$, $R^7$, and $R^8$ are independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl; and $R^4$ is hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, or substituted or unsubstituted heteroalkyl. $R^6$ and $R^7$ can optionally combine to form substituted or unsubstituted aryl or substituted or unsubstituted heteroaryl. In this class of compounds, if ===== is a double bond, $A^1$, $A^2$, $A^4$, $A^5$, $A^6$, $A^7$, $A^8$, and $A^{10}$ are CH, $A^3$ is —CCO$_2$H, $R^4$, $R^7$, and $R^8$ are each hydrogen, $R^5$ and $R^6$ are methyl, and $R^3$ is cyano, then $A^9$ is not —CBr.

Also provided herein are compositions including one or more compounds as described above and a pharmaceutically acceptable carrier.

Further provided herein are methods of treating or preventing a microbial infection in a subject. In some embodiments, the methods comprise administering to the subject an effective amount of an RNase inhibitor of the following structure:

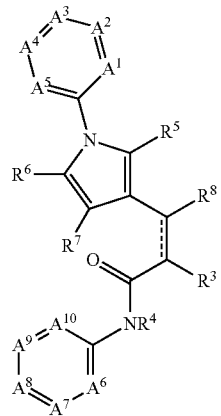

or pharmaceutically acceptable salts or prodrugs thereof. In these compounds, ===== is a single or double bond; $A^1$, $A^2$, $A^3$, $A^4$, and $A^5$, are each independently selected from N or $CR^1$; $A^6$, $A^7$, $A^8$, $A^9$, and $A^{10}$ are each independently selected from N or $CR^2$; each $R^1$, each $R^2$, $R^3$, $R^5$, $R^6$, $R^7$, and $R^8$ are independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl; and $R^4$ is hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, or substituted or unsubstituted heteroalkyl. Optionally, $R^6$ and $R^7$ can combine to form substituted or unsubstituted aryl or substituted or unsubstituted heteroaryl. In some examples, the RNase inhibitor is

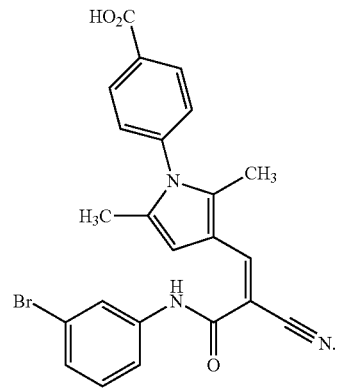 [SMILES: Cc1cc(/C=C(/C#N)C(=O)Nc2cccc(Br)c2)c(C)n1-c1ccc(C(=O)O)cc1]

In some embodiments, the microbial infection is a bacterial infection. The bacterial infection can be, for example, a Gram positive bacterial infection. Optionally, the bacterial infection is a *Staphylococcus* infection such as, for example, a *Staphylococcus aureus* infection. The *Staphylococcus aureus* infection can be a drug-resistant *Staphylococcus aureus* infection or a biofilm-associated *Staphylococcus aureus* infection. In some examples, the RNase inhibitor is a RnpA inhibitor. Optionally, the methods can further comprise administering a second compound to the subject, wherein the second compound is an antibacterial compound.

Also provided herein are methods of inhibiting a bacterial ribonuclease comprising contacting the bacterial ribonuclease with an effective amount of an RNase inhibitor. In some embodiments, the RNase inhibitor is a compound of the following structure:

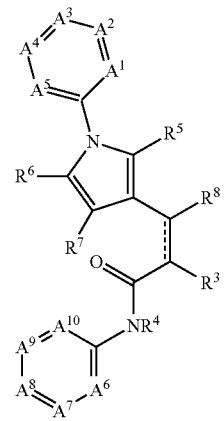

or pharmaceutically acceptable salts or prodrugs thereof. In these compounds, ===== is a single or double bond; $A^1$, $A^2$, $A^3$, $A^4$, and $A^5$, are each independently selected from N or $CR^1$; $A^6$, $A^7$, $A^8$, $A^9$, and $A^{10}$ are each independently selected from N or $CR^2$; each $R^1$, each $R^2$, $R^3$, $R^5$, $R^6$, $R^7$, and $R^8$ are independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl; and $R^4$ is hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, or substituted or unsubstituted heteroalkyl. Optionally, $R^6$ and $R^7$ combine to form substituted or unsubstituted aryl or substituted or unsubstituted heteroaryl.

Optionally, the bacterial ribonuclease is the protein component of *Staphylococcus aureus* RNase P (e.g., RnpA). The contacting can occur, for example, in vivo or in vitro.

Further provided herein are methods of identifying a compound for treating or preventing a microbial infection. The method includes the steps of combining RNA, RnpA, and a fluorescent dye to form a mixture; contacting the mixture with the compound; and monitoring RnpA-mediated total bacterial RNA degradation in the cell using fluorescence, wherein decreased fluorescence, as compared to a control, indicates RNA degradation. In this method, a compound that decreases the RnpA-mediated total bacterial RNA degradation, as compared to a control, is identified as the compound for treating or preventing the microbial infection.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

FIG. 1 is a graph showing the percent of detectable mRNA species (Y-axis) with a half life of ≤2.5, 5, 15, 30, or >30 min during exponential- and/or stationary-phase growth (X-axis).

FIG. 2 demonstrates that *S. aureus* RnpA catalyzes rRNA and mRNA digestion. Panel A is an SDS-PAGE of purified recombinant *S. aureus* RnpA; shown are molecular markers (Lanes M), 2.5 µg and 25 µg elution products (Lanes 1 and 2, respectively). Panel B depicts the gel-mobility of 1 µg of total *S. aureus* RNA following 60 min incubation in the absence (−) or presence (+) of 50 pmol of each putative ribonuclease (indicated) in 1× reaction buffer (2 mM NaCl, 2 mM $MgCl_2$, 50 mM Tris-HCl, pH 6.0). Panel C displays the mobility of 0.5 pmol in vitro transcribed spa mRNA following 60 min incubation in the absence (0 pmol) or presence of the indicated amount of RnpA protein in 1× reaction buffer. Molecular weight markers (M) are shown. Panel D shows reverse-transcription mediated PCR products of 2 µg of in vitro transcribed spa mRNA in the absence (−) or presence (+) of 50 pmol RnpA or RNase J1 and in the absence (serum alone) or presence of 1, 2.5, 5, 10, or 20 µg RnpA polyclonal antibody. Panel E shows plotted measurements for all mRNA species measured on a GeneChip at 0 (X-axis) and 10 min (Y-axis) post-transcriptional arrest. Grey dashed line indicates the lower limit of sensitivity for each sample.

DETAILED DESCRIPTION

Figure 3:
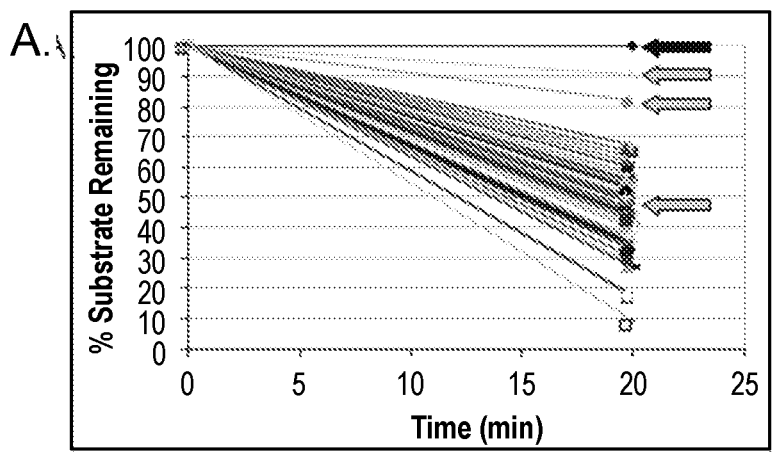
FIG. 3, Panel A shows representative screening effort results. Panel B shows an agarose gel-based assay depicting the gel mobility of molecular weight marker, spa mRNA in the absence (−) or presence (+) of 20 pmol RnpA and RnpA-mediated spa mRNA degradation in the presence of increasing concentrations of RNPA1000. Panel C shows the structure of RnpA-inhibitory molecule RNPA1000.
Figure 3:
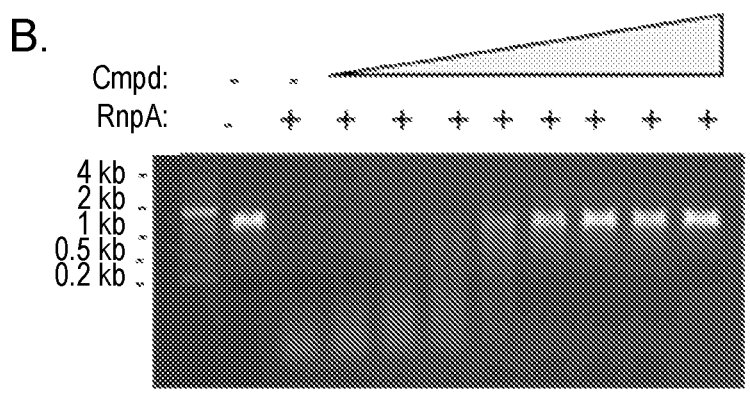
Figure 3:
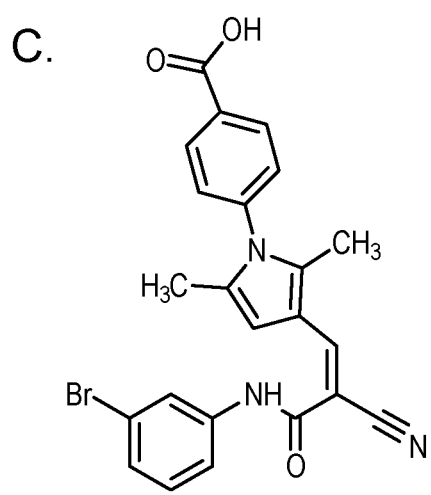

Provided herein are small molecule inhibitors of bacterial RnpA associated ribonuclease (RNase) activity, methods of their preparation, and methods of their use in treating and preventing microbial infections. The small molecule inhibitors exploit a novel mechanism of treating microbial infections, such as *Staphylococcus aureus*, which involves the essential *S. aureus* protein, RnpA, catalyzing rRNA and mRNA digestion. This mechanism has not previously been known or developed. Exploiting this activity, high throughput and secondary screening assays were employed to identify small molecule inhibitors of RnpA-mediated RNA degradation. These agents limited cellular mRNA degradation and exhibited antimicrobial activity against several microbes, including predominant methicillin-resistant *S. aureus* (MRSA) lineages circulating throughout the U.S., vancomycin intermediate susceptible *S. aureus* (VISA), vancomycin resistant *S. aureus* (VRSA) and other Gram-positive bacterial pathogens with high RnpA amino acid conservation (see McDougal et al., *J Clin Microbiol*, 41: 5113-5120 (2003)). As provided herein, the RnpA-inhibitors limit disease in a systemic mouse infection model and have antimicrobial activity against biofilm-associated *S. aureus*. Taken together, these findings indicate that RnpA plays a role in *S. aureus* RNA degradation, demonstrate that high through-put screening can be used to identify mRNA turn-over inhibitors, and provide proof of principle for RNA catabolism-based antimicrobial therapy.

The materials, compounds, compositions, articles, and methods described herein may be understood more readily by reference to the following detailed description of specific aspects of the disclosed subject matter and the Examples included therein.

Before the present materials, compounds, compositions, kits, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., bacterial infection). It is understood that this is typically in relation to some standard or expected value, in other words it is relative, but that it is not always necessary for the standard or relative value to be referred to. For example, "reduces bacterial infection" means reducing the spread of a bacterial infection relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., bacterial infection). The term "control" is used synonymously with the term "treat."

By "antimicrobial" is meant the ability to treat or control (e.g., reduce, prevent, inhibit, or eliminate) the growth of a microbe at any concentration. Similarly, the term "antibacterial" refers to the ability to treat or control cellular bacteria growth at any concentration.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a nonaromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like.

When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as ($Z^1Z^2$)C=C($Z^3Z^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O.

The terms "amine" or "amino" as used herein are represented by the formula —NZ$^1$Z$^2$, where Z$^1$ and Z$^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O.

The term "ester" as used herein is represented by the formula —OC(O)Z$^1$ or —C(O)OZ$^1$, where Z$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula A$^1$OA$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula Z$^1$C(O)Z$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —NO$_2$.

The term "silyl" as used herein is represented by the formula —SiZ$^1$Z$^2$Z$^3$, where Z$^1$, Z$^2$, and Z$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$Z$^1$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples.

Compounds

The small molecule inhibitors of bacterial ribonuclease (RNase) described herein include compounds represented by Formula I:

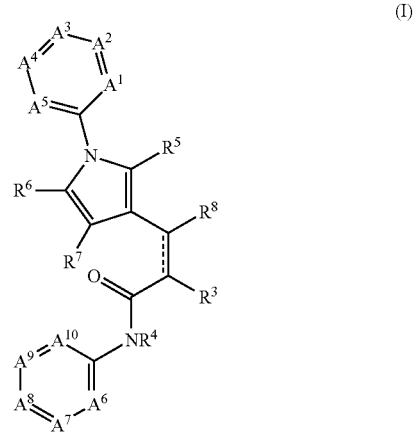

(I)

and pharmaceutically acceptable salts and prodrugs thereof.

In Formula I, ═════ is a single or double bond.

Also in Formula I, $A^1$, $A^2$, $A^3$, $A^4$, and $A^5$ are each independently selected from N or $CR^1$. Each $R^1$ can be independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl. Optionally, one or more of $A^1$, $A^2$, $A^3$, $A^4$, and $A^5$ is CH. In some embodiments, $A^3$ is —$CCO_2H$.

Additionally in Formula I, $A^6$, $A^7$, $A^8$, $A^9$, and $A^{10}$ are each independently selected from N or $CR^2$. Each $R^2$ can be independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl. Optionally, one or more of $A^6$, $A^7$, $A^8$, $A^9$, and $A^{10}$ is CH. In some embodiments, $A^9$ is CBr. In some embodiments, $A^8$ is CBr.

Also in Formula I, $R^3$, $R^5$, $R^6$, $R^7$, and $R^8$ are independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl. Optionally, $R^3$ is cyano. In some embodiments, $R^5$ and $R^6$ are methyl.

Further in Formula I, $R^4$ is hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, or substituted or unsubstituted heteroalkyl.

In Formula I, adjacent R groups, e.g., $R^6$ and $R^7$, can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. For example, $R^6$ can be a substituted or unsubstituted ethylene group and $R^7$ can be a substituted or unsubstituted propylene group that combine to form a substituted or unsubstituted phenyl. In these examples, $R^6$ and $R^7$ combine to form Structure I-A, i.e., the indole embodiments:

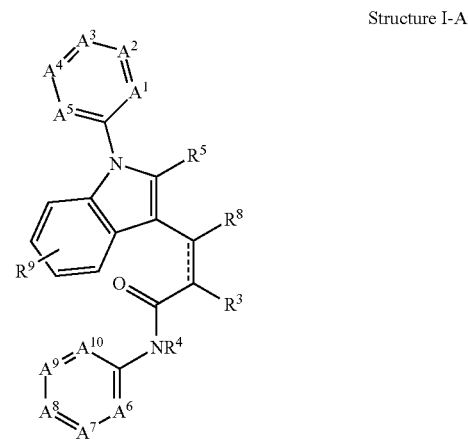

Structure I-A

Optionally, the phenyl ring of the indole in Structure I-A can be substituted with $R^9$. In Structure I-A, $R^9$ is selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, or substituted or unsubstituted carboxyl.

In some examples of Formula I, each of $A^1$, $A^2$, $A^3$, $A^4$, and $A^5$ are CH to form Structure I-B. In other examples of Formula I, each of $A^6$, $A^7$, $A^8$, $A^9$, and $A^{10}$ are CH to form Structure I-C. In still other examples of Formula I, each of $A^1$, $A^2$, $A^3$, $A^4$, $A^5$, $A^6$, $A^7$, $A^8$, $A^9$, and $A^{10}$ are CH to form Structure I-D.

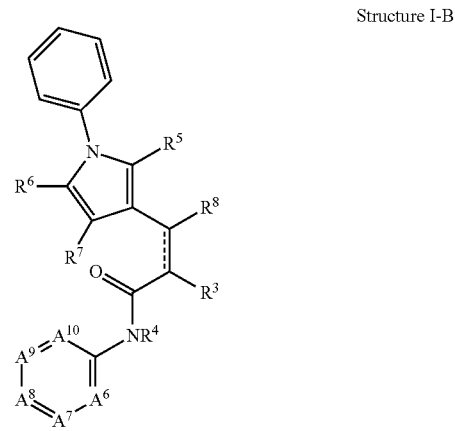

Structure I-B

Structure I-C

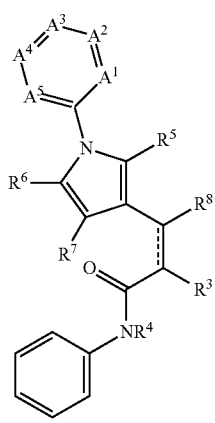

Structure I-D

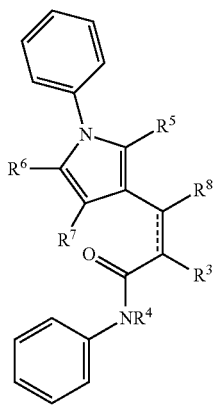

Optionally, the compound according to Formula I includes an enone and is a compound according to Structure I-E. In some embodiments, the enone is reduced to form a compound according to Structure I-F.

Structure I-E

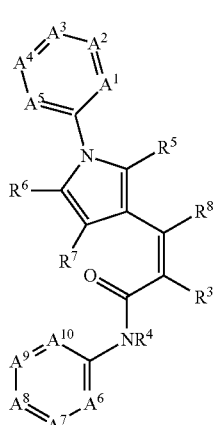

Structure I-F

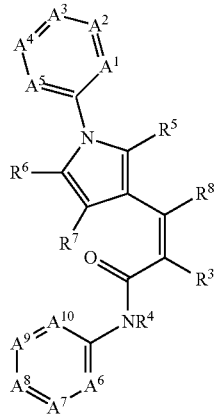

In some embodiments, $A^3$ in Formula I is —$CCO_2H$ as shown in Structure I-G:

Structure I-G

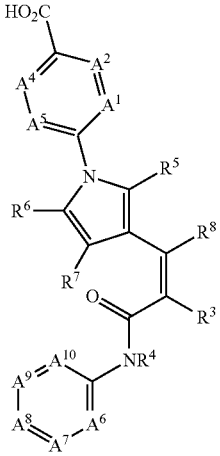

In some examples of Formula I, if ===== is a double bond, $A^1$, $A^2$, $A^4$, $A^5$, $A^6$, $A^7$, $A^8$, and $A^{10}$ are CH, $A^3$ is —$CCO_2H$, $R^4$, $R^7$, and $R^8$ are each hydrogen, $R^5$ and $R^6$ are methyl, and $R^3$ is cyano, then $A^9$ is not —CBr.

A particular example of Formula I is compound RNPA-1000:

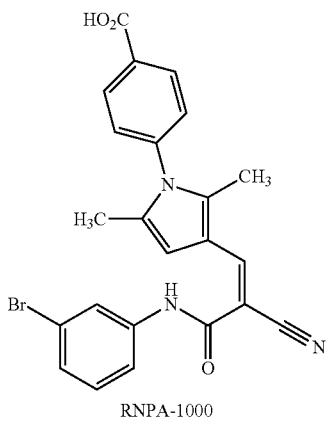

RNPA-1000

Pharmaceutical Compositions

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection can comprise physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as can be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught herein.)

Administration of the compounds and compositions described herein or pharmaceutically acceptable salts thereof to a subject can be carried out using therapeutically effective amounts of the compounds and compositions described herein or pharmaceutically acceptable salts thereof as described herein for periods of time effective to treat a disorder.

The effective amount of the compounds and compositions described herein or pharmaceutically acceptable salts thereof as described herein can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. The expression effective amount, when used to describe an amount of compound in a method, refers to the amount of a compound that achieves the desired pharmacological effect or other effect, for example an amount that results in bacterial enzyme inhibition.

Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Methods of Making the Compounds

The compounds described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on Formula I include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Analogs of RNAP1000 with various diversity groups can be prepared using a number of known synthetic schemes (Jendralla et al., *J. Med. Chem.*, 33(1): 61-70 (1990)), including the reaction steps shown in Scheme 1. The condensation shown in Step 1 can be accelerated using microwave technology (He et al., *J. Org. Chem.*, 7:1150-1157 (2011)). Incorporation of a leaving group such as bromo into the $R^1$ position shown in Scheme 1 allows for further homologation via transition metal-catalyzed chemistry such as Suzuki and Buchwald condensations. Mixtures of stereoisomers might be expected from the Knoevenagal reaction shown in Step 3, but the isomers can be separated via chromatography and the corresponding (Z)- and (E)-isomers can be separately converted to final targets, enhancing the diversity set.

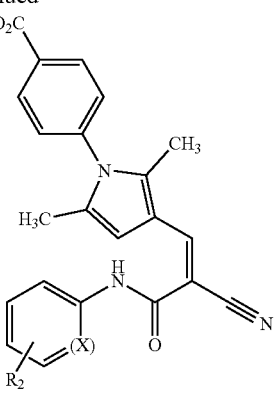

Additional diversity can be obtained by varying the reagents in the general scheme. Substitution of propane-2, 5-dione with homologous diones will allow for exploration of additional binding interactions adjacent to the pyrrole core (Scheme 2). The Vilsmeier-Haack formylation can give a mixture of regioisomers, which can be separated by chromatography (Manetti et al., *Chem Med Chem*, 1(9): 973-989 (2006)) and converted separately to final target compounds. Indole analogs can be prepared from known indole-3-carboxaldehydes using an analogous scheme (Khan et al., *Journal of Heterocyclic Chemistry*, 16(5): 997-999 (1979)).

Scheme 1:

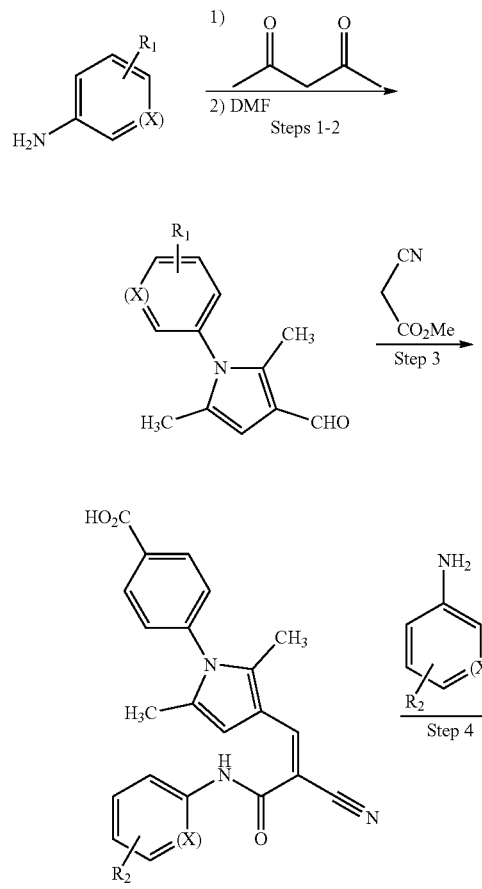

Scheme 2:

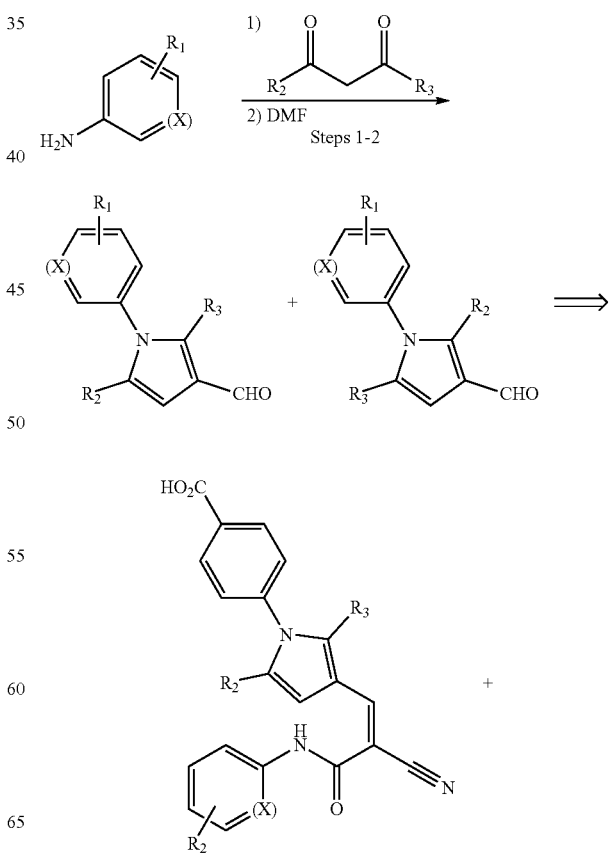

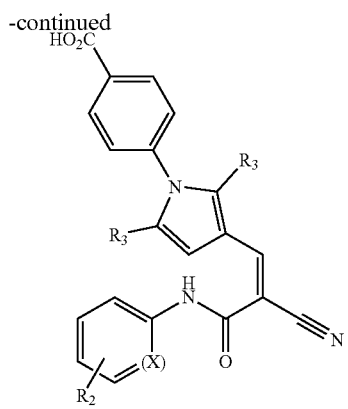

The role of the nitrile can be investigated by substituting malononitrile with a protected malonic diester that is resistant to transamination, such as the t-butyl ester shown in Scheme 3. Deprotection provides the intermediate acid, which can be further elaborated to explore the SAR around that region of the molecule. Finally, reduction of the double bond of the adduct obtained from the Knoevenagal reactions (e.g., Scheme 3, step 3) provides analogs with and without enone moieties. Racemic mixtures can be tested by chiral HPLC, and subsequently separated.

Scheme 3:

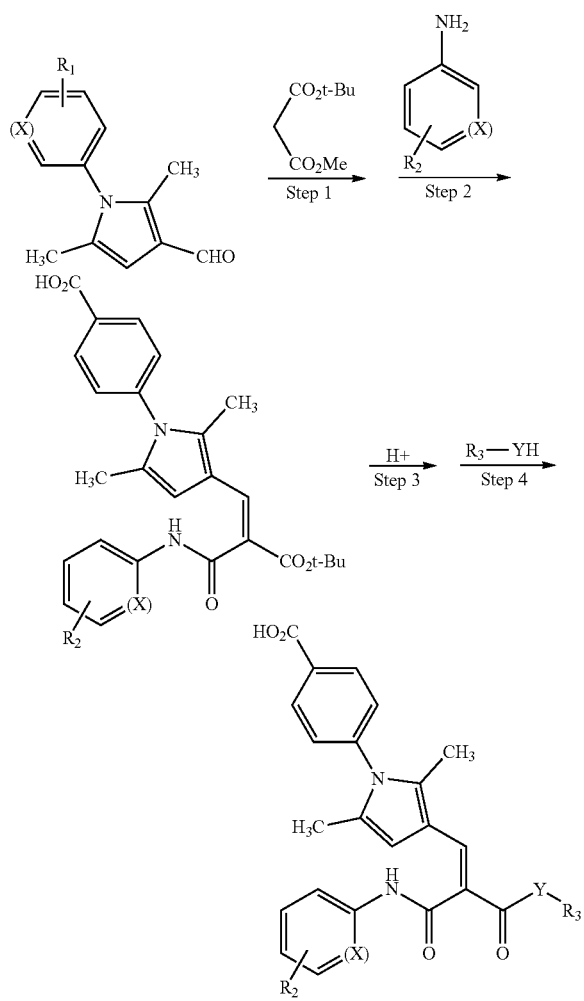

Activity Assays

Provided herein are methods of identifying a compound for treating or preventing a microbial infection. The methods can include preparing a compound or composition as described herein and assaying the inhibitory activity of the compound or composition against bacterial ribonucleases, such as RNase P. RNase P is an ubiquitous enzyme that catalyzes maturation of the 5' end of precursor tRNAs (see Frank et al., Annu Rev Biochem, 67: 153-180 (1998); Kazantsev et al., Nat Rev Microbiol, 4: 729-740 (2006); Walker et al., Crit Rev Biochem Mol Biol, 41: 77-102 (2006)). The enzyme is unique by virtue of the fact that it is a ribonucleoprotein complex, which includes a single ribozyme RNA molecule and at least one protein component. Within bacteria both the ribozyme (rnpB) and protein (RnpA) components are required for cell viability; rnpB mediates tRNA processing in vitro, whereas no function has been firmly established for RnpA (see Gossringer et al., J Bacteriol, 188: 6816-6823 (2006); Schedl et al., Proc Natl Acad Sci USA, 70: 2091-2095 (1973); Waugh et al., J Bacteriol, 172: 6316-6322 (1990)). Domain searches (see Letunic et al., Nucleic Acids Res, 34: D257-260 (2006); Schultz et al., Proc Natl Acad Sci USA, 95: 5857-5864 (1998)) revealed that S. aureus RnpA residues 40-111 best conform to a ribonuclease-like motif. Further, several RNA binding sites are embedded within this region (see Spitzfaden et al., J Mol Biol, 295: 105-115 (2000)). E. coli and B. subtilis RNase P have been found to digest certain double-stranded RNA templates, such as guide-RNAs and 4.5s RNA (see Lundblad et al., Proc Natl Acad Sci USA, 105: 2354-2357 (2008)). Cleavage of those templates strictly requires RnpA (see Liu et al., Cell, 77: 1093-1100 (1994); Marvin et al., J Cell Biochem, 108: 1244-1251 (2009)). As provided herein, RNase P mediated RNA digestion may be dependent on rnpB, RnpA, or both. Thus, RnpA modulates S. aureus RNA degradation.

RNA degradation can be used to identify compounds suitable inhibiting bacterial ribonucleases, and thus, suitable for treating or preventing a microbial infection. In some embodiments, a fluorescence based assay can be used to identify the compounds. The method can include the steps of combining RNA, RnpA, and a fluorescent dye to form a mixture, contacting the mixture with the compound, and monitoring RnpA-mediated total bacterial RNA degradation in the cell using fluorescence. Decreased fluorescence, as compared to a control, indicates RNA degradation. As used herein, decreased fluorescence refers to a lowering of fluorescence, as compared to a control, of at least about 1%. For example, decreased fluorescence can be a decrease in fluorescence of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%, as compared to a control. A compound that decreases the RnpA-mediated total bacterial RNA degradation, as compared to a control, can be identified as the compound for treating or preventing the microbial infection. A suitable fluorescent dye for use in the methods described herein includes Quant-iT RiboGreen® (Invitrogen; Carlsbad, Calif.).

In some examples, compounds can be further assayed using the Mueller Hinton (MH) broth antibacterial assay as specified by the Clinical and Laboratory Standards Institute MIC broth microdilution protocol (see Methods for Dilution Antimicrobial Susceptibility Tests for Bacteria That Grow Aerobically; Approved Standard, In *The Clinical and Laboratory Standards Institute* (*CLSI*, formerly *NCCLS*), 7th ed., January 2006, 26 (2), M7-A7; see also Performance Standards for Antimicrobial Susceptibility Testing; Eighteenth Informational Supplement, In *The Clinical and Laboratory Standards Institute* (*CLSI*, formerly *NCCLS*), January 2008, 28 (1), M100-S18).

The activity of the compounds and compositions provided herein as inhibitors of bacterial RNase can be measured in standard assays, e.g., HPLC assays. The compounds can be tested as inhibitors of bacterial RNase in a bacterial RNase enzyme assay. Compounds that are identified as bacterial RNase inhibitors are useful in treating or preventing microbial infections. The activities of the compounds and compositions as determined using the assays can be reported in terms of $IC_{50}$. As used herein, $IC_{50}$ refers to an amount, concentration, or dosage of a particular test compound that achieves a 50% inhibition of a maximal response in an assay that measures such response.

In certain aspects, the disclosed compounds and compositions need not actually be synthesized, but instead can be used as targets for any molecular modeling technique to predict and characterize interactions with bacterial RNase. This is achieved through structural information and computer modeling. Computer modeling technology allows visualization of the three-dimensional atomic structure of a selected molecule and the rational design of new compounds that will interact with the enzyme. The three-dimensional construct of the enzyme typically depends on data from x-ray crystallographic analyses or NMR imaging of the selected molecule. This data is available for bacterial RNase. The molecular dynamics require force field data (e.g., Merck Molecular Force Field). The computer graphics systems enable prediction of how a new compound will link to the enzyme and allow experimental manipulation of the structures of the compound to perfect binding specificity. Prediction of what the interactions will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other. Upon identification of compounds that interact in a desired way with bacterial RNase in silico, actual compounds can be synthesized and assayed as disclosed herein.

Methods of Use

Provided herein are methods to treat, prevent, or limit microbial infections in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating microbial infections and cancer in humans, e.g., pediatric and geriatric populations, and in animals, e.g., veterinary applications. Microbial infections include, for example, bacterial and fungal infections. Bacterial infections include infections caused by bacilli, cocci, spirochaetes, and *vibrio* bacteria. In some examples, the microbial infection is a bacterial infection (e.g., a Gram positive bacterial infection). In some examples, the bacterial infection is *Staphylococcus* infection, such as a *Staphylococcus aureus*. The compounds and compositions described herein are useful in treating a variety of *Staphylococcus aureus* infections, including drug-resistant *Staphylococcus aureus* infections and biofilm-associated *Staphylococcus aureus* infections. In some embodiments, the *Staphylococcus aureus* infection is methocillin-resistant *S. aureus* (*S. aureus* MRSA). In other embodiments, the *Staphylococcus aureus* infection is vancomycin-resistant *S. aureus*. Optionally, the *Staphylococcus aureus* infection is multi-drug resistant. In some examples, the compounds and compositions described herein can be used to treat *Bacillus* infections (e.g., *Bacillus anthracis* and *Bacillus cereus*), *Streptococcus* infections (e.g., *Streptococcus pneumoniae* and *Streptococcus pyogenes*), and *Enterococcus* infections (e.g., *Enterococcus faecalis* and vancomycin-resistant *Enterococcus*).

The methods of treatment or prevention described herein can further include treatment with one or more additional agents (e.g., an antibacterial agent). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents. For example, the compounds or compositions or pharmaceutically acceptable salts thereof as described herein can be combined into a pharmaceutical composition with an additional antibacterial agent, such as acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; Lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin; oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillin G benzathine; penicillin G potassium; penicillin G procaine; penicillin G sodium; penicillin V; penicillin V benzathine; penicillin V hydrabamine; penicillin V potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin B sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; or zorbamycin.

Further provided herein are methods of inhibiting a bacterial ribonuclease, such as the protein component of *Staphylococcus aureus* RNase P. In some embodiments, the bacterial ribonuclease is RnpA. The methods comprise contacting the bacterial ribonuclease with an effective amount of one or more of the compounds or compositions described herein. Such amounts are sufficient to achieve a therapeutically effective concentration of the compound or active component of the composition in vivo or in vitro.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of a bacterial infection), during early onset (e.g., upon initial signs and symptoms of a bacterial infection), or after an established inflammatory response or development of a bacterial infection. Prophylactic administration can occur for several days to years prior to the manifestation of symptoms of an infection. Prophylactic administration can be used, for example, in the preventative treatment of subjects exposed to *Staphylococcus aureus*. Therapeutic treatment involves administering to a subject a therapeutically effective amount of the compounds and compositions or pharmaceutically acceptable salts thereof as described herein after a bacterial infection is diagnosed.

Kits

Also provided herein are kits for treating or preventing inflammation or cancer in a subject. A kit can include any of the compounds or compositions described herein. For example, a kit can include a compound of Formula I. A kit can further include one or more antibacterial agents (e.g., oxacillin). A kit can include an oral formulation of any of the compounds or compositions described herein. A kit can additionally include directions for use of the kit (e.g., instructions for treating a subject).

The examples below are intended to further illustrate certain aspects of the methods and compounds described herein, and are not intended to limit the scope of the claims.

EXAMPLES

S. aureus RNA degradation factors were empirically identified and, as demonstrated below, were proven to represent promising antimicrobial drug development targets. To do so, the fact that S. aureus owes its ability to cause infection, in part, to the temporal expression of an expansive repertoire of virulence factors, many of which are regulated in a cell density-dependent manner during laboratory culture conditions, was exploited (see Novick, R. P., Mol Microbiol, 48: 1429-1449 (2003)). Studies were then performed to determine whether growth phase regulated changes in S. aureus virulence factor expression occur at the level of mRNA degradation and whether the proteins involved in this process may include members of the organism's RNA degradation machinery. Accordingly, Affymetrix GeneChips were used to compare the mRNA decay rates of well-characterized S. aureus virulence factors during exponential- and stationary-phase growth.

Results revealed that the mRNA turnover properties of many S. aureus virulence factor transcripts differed between the two growth phases. Furthermore, the global mRNA decay properties of exponential and stationary phase cells were found to be dramatically different; 884 S. aureus mRNA species were stabilized during stationary phase growth. Among the genes whose expression correlated with mRNA decay was the protein component of ribonuclease P, RnpA, suggesting that it may play a role in bulk mRNA turnover. Consistent with that possibility, it was demonstrated that recombinant S. aureus RnpA exhibits ribonuclease activity in vitro and RnpA depleted cells exhibit reduced mRNA degradation. Because RnpA is an essential S. aureus enzyme with low amino acid conservation with mammalian proteins, it is an appropriate target for antimicrobial drug discovery. Accordingly, high through-put and secondary screening assays were used to identify small molecule inhibitors of RnpA-mediated RNA degradation. One of these agents was shown to inhibit S. aureus mRNA turnover, exhibited antimicrobial activity against MRSA, VISA, and VRSA, as well as other Gram-positive pathogens with high RnpA conservation, and limited pathogenesis in a murine acute lethal model of infection. Collectively these results demonstrate that RnpA is a previously uncharacterized member of the S. aureus RNA degradation machinery and validate its utility as an antimicrobial drug discovery target.

Example 1

Growth-phase Dependent Alternations in S. aureus Turnover

For half life determinations, S. aureus strain UAMS-1, RN4220 (pCN51; plasmid containing $CdCl_2$ inducible promoter), RN4220 (pRNPA; pCN51 capable of producing full length rnpA mRNA), or RN4220 (pRNPA-A.S.; pCN51 capable of producing rnpA antisense RNA) were grown to mid-exponential or stationary phase, transcription was arrested by the addition of rifampin (200 µg/ml), and aliquots were removed at 0-, 2.5-, 5-, 15- and 30-min post-transcriptional arrest for strain UAMS-1. To conserve reagents, aliquots were removed at 0 and 10 min post-transcriptional arrest for RN4220 derivatives. Plating ensured cultures had not developed rifampin resistance. Each strain and/or growth phase was assessed twice, except for RN4220 pRNPA-A.S. cells which were assessed four times. RNA was isolated from each aliquot, labeled, hybridized to an S. aureus GeneChip (Affymetrix; Santa Clara, Calif.), duplicates were averaged, and the mRNA half-lives of all mRNA species were determined, as previously described (see Anderson et al., J Bacteriol, 188: 6739-6756 (2006); Roberts et al., J Bacteriol, 188: 2593-2603 (2006)). To measure the mRNA turnover characteristics of RNPA1000 challenged cells, exponential-phase S. aureus were treated with 0.5×MIC of the RnpA inhibitor or equivalent volume compound solvent (DMSO) for 30 min. Transcript synthesis was then arrested and the transcript titers of mRNA species were measured at 0- and 5-min post-transcriptional arrest (see Anderson et al., J Bacteriol, 188: 6739-6756 (2006); Roberts et al., J Bacteriol, 188: 2593-2603 (2006)).

The results demonstrated that the mRNA turnover properties of many (41%) virulence factor transcripts differed between the two growth phases, suggesting that regulated changes in mRNA turnover may affect their expression. Moreover, it was observed that the organism produced at least five stationary phase specific small stable RNAs (SSRs), a hypothesized class of regulatory non-coding RNA molecules (see Anderson et al., J Bacteriol, 188: 6739-6756 (2006); Roberts et al., J Bacteriol, 188: 2593-2603 (2006)). Further, the global mRNA turnover properties of exponential- and stationary-phase cells differed considerably. Consistent with previous measurements, it was found that most (90%) exponential phase transcripts are rapidly degraded (half life of ≤5 min), 9% exhibit intermediate stability (half life of >5 min but ≤30 min), and 1% are stable (half life of ≥30 min) (see Anderson et al., J Bacteriol, 188: 6739-6756 (2006); Roberts et al., J Bacteriol, 188: 2593-2603 (2006)). However, during stationary phase growth, 76%, 21%, and 3% of mRNA species exhibit short, intermediate, and stable half lives, respectively (FIG. 1). Neither RNase J1 nor RNase Y were found to be differentially expressed in a growth phase dependent manner. Among the 367 genes repressed during stationary phase growth was rnpA, which codes for the protein component of ribonuclease P.

Example 2

S. aureus RnpA Exhibits Ribonuclease Activity and Affects Cellular mRNA Degration Protein Purification Each putative S. aureus ribonuclease predicted open reading frame was PCR amplified and inserted into the ligation-independent cloning site of plasmid pET-30 Ek/LIC (Novagen; Madison Wis.). Sequencing confirmed that this fused a hexahistidine-tag to the N-terminus of each protein under the control of the plasmid's isopropyl β-D-1-thiogalactopyranoside (IPTG) inducible promoter. Following transformation, each protein was purified from E. coli BL21 (DE3) cells grown in the presence of IPTG (4 hr) by $Ni^{+2}$ affinity chromatography. More specifically, 10 g of cell pellet was suspended in 50 ml of buffer A (300 mM NaCl, 50 mM $Na_2HPO_4$, pH 7.4) containing a complete mini EDTA-free protease inhibitor tablet (Roche; Branford, Conn.) and 20 mM imidazole. Cells were ruptured by seven passes at 15,000 psi through an Emulsifex-C3 microfluidizer (Avestin Inc.; Ottawa, Canada). Cell debris was removed by centrifugation at 12,000×g for 30 min and supernatants were loaded onto a 5 mL Ni-NTA FF-crude affinity column (GE Healthcare Bio-Sciences; Piscataway, N.J.) with an AKTA-FPLC high performance liquid chromatography system (GE Healthcare Bio-Sciences; Pittsburgh, Pa.). Proteins eluted in a single peak with a linear imidazole gradient (80 mM to 500 mM) in buffer A. The presence of each protein was assessed by Coomasie stained SDS-PAGE and matrix-assisted laser desportion/ionization (MALDI) analysis spectrometry (Wistar Institute; Philadelphia, Pa.).

Plasmids

Plasmids pRNPA-S and pRNPA-A.S. contain the putative rnpA transcriptional unit including predicted Shine-Delgarno sequence in the sense and antisense orientation, respectively under control of the $CdCl_2$ inducible of the *S. aureus* shuttle-vector pCN51 (see Charpentier et al., *Appl Environ Microbiol*, 70: 6076-6085 (2004)). Briefly, the rnpA open reading frame and 34 nt upstream sequence was PCR amplified from *S. aureus* strain UAMS-1 using primers 5' GAATTCTCAAATAAAAACGATAAATAAGCGAGTGAT GTTA (forward) (SEQ ID NO.8) and 5' GGTACCTTACTTAATCTTTTTATTAAAAACTTTGGCA A (reverse) (SEQ ID NO.9) containing a 5' terminal EcoRI and KpnI restriction enzyme site (underlined), respectively, or primers in which the restriction enzyme sequence had been reversed. Resulting PCR products were ligated into pCRII-TOPO vector and transformed into *E. coli* INVαF' cells for propagation (Invitrogen, Carlsbad, Calif.). Plasmid DNA was subsequently purified using QIAprep Spin Miniprep Kits (Qiagen, Valencia, Calif.) then digested with EcoRI and KpnI to liberate the plasmid inserts, which were gel purified using a QIAquick Gel Extraction Kit (Qiagen) and ligated into EcoRI and KpnI-digested pCN51. DNA sequencing confirmed the integrity of plasmid pRNPA-S and pRNPA-A.S.

Western Blotting

Affinity purified PolyQuik rabbit *S. aureus* RnpA polyclonal antibodies were generated by Invitrogen (Carlsbad, Calif.). Total bacterial proteins were isolated from RN4220 cells containing plasmid vector (pCN51), RnpA overexpressor plasmid (pRNPA-S) or RnpA antisense RNA plasmid (pRNPA-A.S.) following 30 min growth in TSB medium supplemented with 2.5 µM $CdCl_2$ to induce RNA expression and 10 µg/ml erythromycin for plasmid maintenance. Resultant protein concentrations were determined by conventional Bradford Assays and 2.0 µg of each protein sample or purified *S. aureus* RnpA was electrophoresed in a 10% SDS polyacrylamide gel and transferred to a polyvinylidene fluoride membrane (Millipore, Billerica, Mass.). Membranes were blocked with 10% milk, washed, incubated with rabbit RnpA antibody (1:1000 dilution), washed, incubated with horseradish peroxidase-conjugated anti-rabbit antibody (1:1000 dilution; GE Healthcare) and processed using an Amersham ECL Western Blotting System, according to the manufacturer's recommendations (GE Healthcare).

Results

Recombinant *S. aureus* RnpA was found to catalyze digestion of rRNA and staphylococcal protein A (spa) mRNA (FIGS. 2B and 2C), as well as three other mRNA species tested. Other putative *S. aureus* ribonucleases including RNase III, RNase HII, RNase HIII, RNase Y, RNase J1, and BN did not exhibit equivalent RNA degradation activity during these assay conditions (FIG. 2B). SDS-PAGE and matrix-assisted laser desorption/ionization (MALDI) analysis confirmed that the observed ribonuclease activity was associated with the presence of *S. aureus* RnpA (FIG. 2A). In FIG. 2A, the band at about 17.2 kDa (solid arrow; Band 2) was confirmed to be *S. aureus* RnpA by tandem mass spectrometry (Wistar Institute; Philadelphia, Pa.), whereas top-hits for minor contaminants (dashed arrows) were determined to be *E. coli* 50S ribosomal protein L3 (Band 1) or *S. aureus* RnpA polypeptide fragments, corresponding to amino acids 11-107 (Bands 3 and 4) or 12-107 (Band 5). Nonetheless, SDS-PAGE assessment of approximately 1000-fold excess (25 µg) of RnpA purification product used in the aforementioned ribonuclease assays revealed trace amounts of four additional polypeptides within the protein preparation, raising the possibility that contaminating *E. coli* ribonucleases may be present with the RnpA product. MALDI analysis revealed the identity of these proteins to be *E. coli* ribosomal protein L3, and three *S. aureus* RnpA fragments, presumably reflecting proteolytic degradation of full length RnpA during protein preparation as opposed to mature alternative translation products. No *E. coli* ribonucleases were detected, suggesting that the protein preparation's ribonucleolytic activity could be attributed to *S. aureus* RnpA. Moreover, reverse transcriptase mediated PCR revealed that *E. coli* rnpB was undetectable within the preparation, establishing that RnpA ribonuclease activity was not due to the formation of chimeric RNase P molecules consisting of *S. aureus* RnpA and *E. coli* rnpB RNA. Indeed, in vitro synthesized *E. coli* rnpB neither catalyzed *S. aureus* RNA degradation (alone) nor affected the activity of RnpA-mediated RNA digestion during both standard and elevated $Mg^{+2}$ reaction conditions.

While *S. aureus* RNase J1 exhibited low ribonucleolytic activity in the reaction conditions used here, subsequent studies revealed that it is a potent ribonuclease in differing buffering conditions (see Even et al., *Nucleic Acids Res*, 33: 2141-2152 (2005)) and could be used as a control to further evaluate the putative in vitro ribonuclease activity of *S. aureus* RnpA. More specifically, it was assessed whether RnpA-mediated spa mRNA degradation could be inhibited by the addition of affinity purified rabbit polyclonal *S. aureus* RnpA antibodies. Initial studies did not reveal that antibody limited either RnpA or RNase J1 ribonucleolytic activity. However, anticipating that the only a subset of antibodies within the immunoglobulin mixture may recognize RnpA epitope(s) that affect the enzyme's activity, reverse transcription PCR amplification of spa-digested products was used as a more sensitive means of monitoring what, if any, effect the antibody had on RnpA-mediated transcript degradation. Results revealed that antibody addition did indeed weakly inhibit RnpA-mediated degradation of full length spa mRNA but had no effect on RNase J1 activity (FIG. 2D). Equivalent amounts of pre-immune serum had no effect on RnpA activity. Taken together, these data suggest that a previously unrecognized function *S. aureus* RnpA is that of RNA digestion.

Figure 5:
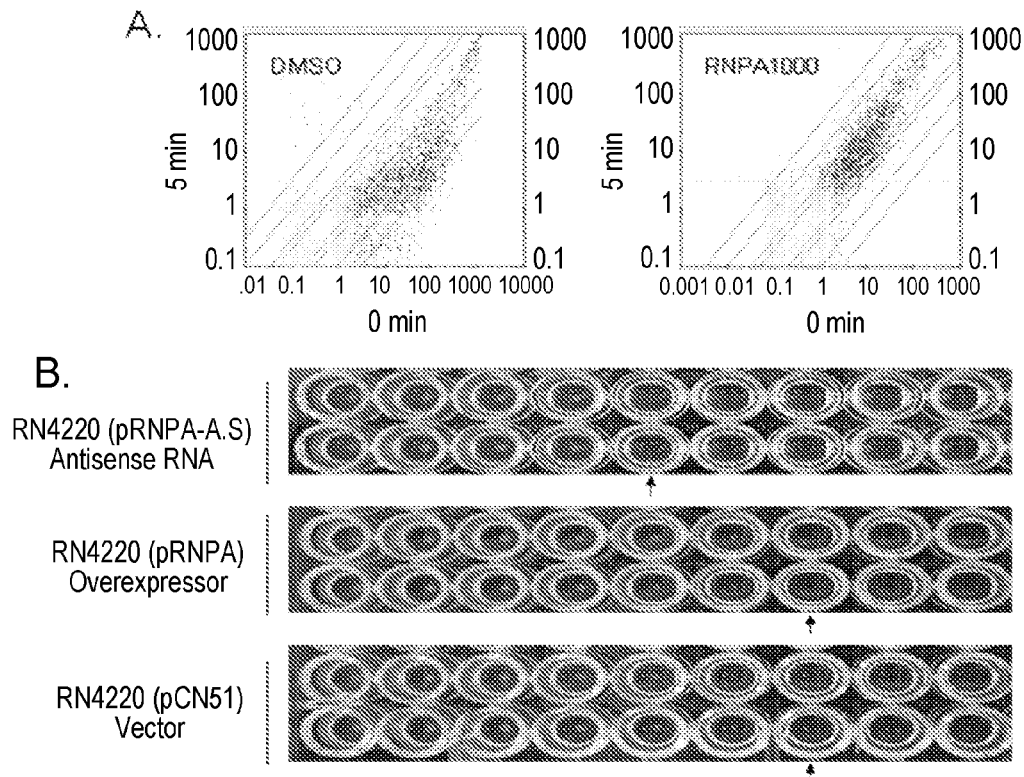
FIG. 5 depicts a plot of all GeneChip detected transcript levels at 0 and 5 min post-transcriptional arrest. Grey dashed line indicates the lower limit of sensitivity for each sample. Panel A shows a comparison of the mRNA levels of DMSO treated cells (Left Panel) and a comparison of the mRNA levels of cells challenged with sub-inhibitory concentration of RnpA-inhibitor (Right Panel). Panel B shows a microtiter plate assay illustrating the in vitro antimicrobial effects of indicated concentration of RNPA1000 (across top) against *S. aureus* RN4220 pRNPA-A.S. (RnpA depleted cells; top panel), RN4220 pRNPA (RnpA overexpressor cells; center panel) and RN4220 pCN51 (vector; bottom panel) when grown in the presence of 2.5 µM $CdCl_2$. All strains were assessed twice; arrows indicate MIC values.
Figure 6:
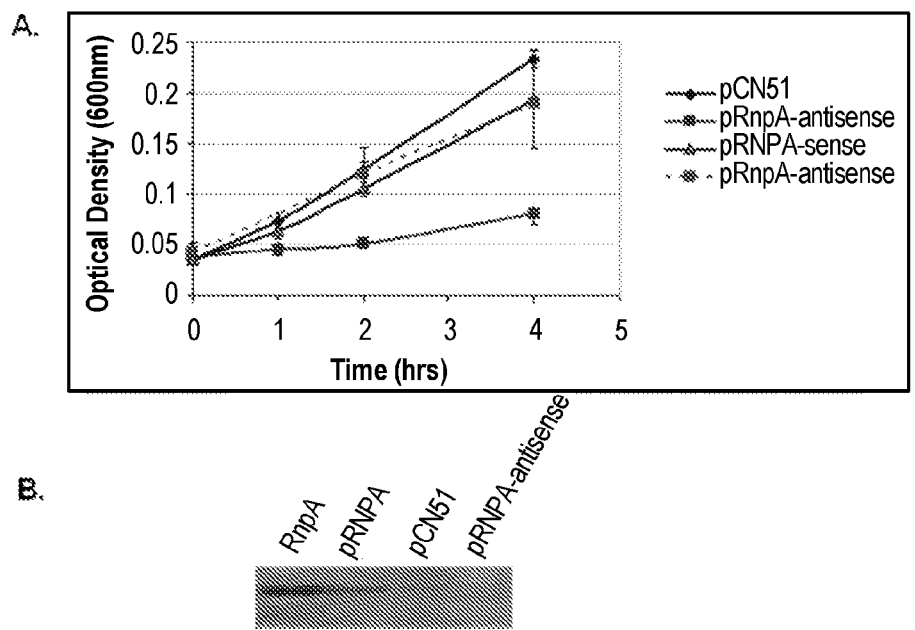
FIG. 6, Panel A depicts plots of the growth characteristics (optical density; Y-axis), for *S. aureus* strain RN4220 containing vector (pCN51; diamonds), rnpA sense RNA (pRNPA-S; triangles) and rnpA antisense RNA (pRNPA-A.S.; squares) when grown in the presence of 10 µM $CdCl_2$. Panel B shows the Western blotting results for *S. aureus* strain RN4220 pCN51 (vector), RN4220 pRNPA (overexpressor), and RN4220 pRNPA-A.S. (RnpA depleted) cells grown in the presence of 2.5 µM $CdCl_2$.

Small molecule inhibitors of essential bacterial RNA turnover proteins are expected to interfere with bacterial growth and represent a new class of antimicrobial agents. In that regard, *S. aureus* RnpA is a reported essential enzyme (see Chaudhuri et al., *BMC Genomics*, 10: 291 (2009); Ji et al., *Science*, 293: 2266-2269 (2001)) and thus could be considered a target for chemotherapeutic development. Indeed, induction of an antisense RNA molecule that is predicted to be complementary to the −34 to +353 rnpA mRNA translation start site (under control of the cadmium chloride inducible promoter of plasmid, pCN51 (see Charpentier et al., *Appl Environ Microbiol*, 70: 6076-6085 (2004)) limited *S. aureus* proliferation in the presence of 10 µM inducer. Conversely, no growth defects were observed for cells expressing the corresponding sense strand RNA molecule or the antisense plasmid strain in the absence of inducer (FIG. 6). These results indicate that *S. aureus* RnpA is an essential protein. Further, using this rnpA antisense RNA system, it was assessed whether RnpA affects *S. aureus* cellular mRNA turnover. Accordingly, the RNA degradation properties were measured for cells harboring plasmid vector alone or cells containing plasmid borne copies of rnpA mRNA or rnpA antisense RNA during growth in the presence of 2.5 µM CdCl$_2$. As shown in FIG. 6, 2.5 µM cadmium chloride was empirically determined to be the optimal concentration that allowed increased- or decreased-RnpA production within rnpA mRNA or rnpA antisense expressing strains, respectively, but did not limit bacterial growth of the antisense RNA producing strain. Accordingly, RNA turnover analyses revealed that diminished RnpA levels correlated with the stabilization of many mRNA species, suggesting that the enzyme contributes to bulk cellular RNA degradation. More specifically, it was found that 88% and 87% of all exponential phase transcripts produced in RnpA overexpressing and vector containing cells exhibited a half life of less than 10 min, respectively. The finding that RnpA overexpression did not accelerate cellular RNA degradation may indicate that the protein's RNA degradation activity is dependent on co-factors, which remain at wild type levels or that the protein did not reach a concentration that effectively increases RNA turnover. Regardless, 63% of transcripts produced in RnpA depleted cells exhibited a half life of less than 10 min, suggesting that the protein contributes to S. aureus mRNA turnover (FIG. 5A).

Example 3

Identification of Small Molecule Inhibitors of RnpA-mediated RNA Degradation

The above results indicate that S. aureus RnpA is an essential enzyme that exhibits in vitro ribonuclease activity and participates in cellular RNA degradation. Moreover, the protein is well conserved across Gram-positive bacteria but lacks amino acid conservation with mammalian proteins, making it an attractive target for novel antibiotic drug development. Accordingly, a fluorescence-based high through-put assay was used to screen 29,066 commercial compounds (ActiProbe-25K and Natural product libraries; Timtec; Newark, Del.) for small molecule inhibitors of RnpA-mediated RNA degradation (FIG. 3A).

Specifically, members of the ActiProbe-25K and Natural Product libraries (29,940 compounds total; TimTec Inc.; Newark, Del.) were screened for small molecule inhibitors of S. aureus RnpA mediated total bacterial RNA degradation. All reactions (50 µl) were performed in 96-well format and contained 20 pmol RnpA, 200 ng S. aureus total RNA, and about 5 µM of each compound in 1× reaction buffer (2 mM NaCl, 2 mM MgCl$_2$, 50 mM Tris-HCl, pH 6.0). Mixtures were incubated at 37° C. for 20 min at which time Quant-iT RiboGreen® (100 µl; Invitrogen) was added to quantify the amount of RNA substrate remaining Percent enzyme inhibition was calculated as remaining substrate/starting substrate*100. For inhibitory titration assays, 1 pmol of spa mRNA was incubated with 20 pmol RnpA alone (positive control) or in the presence of increasing amounts (0, 25, 50, 100, 125, 150, 200, 250, and 500 µM) RNP1000 for one hour at 37° C. Following this, 20 µl of each reaction mixture were subjected to electrophoresis in a 1.2% formaldehyde-containing agarose gel and visualized by ethidium bromide staining.

In total, fourteen molecules inhibited the enzyme's RNA turnover activity by >50%. A gel-based secondary assay confirmed that five of these molecules were bona-fide inhibitors of RnpA-mediated RNA degradation (FIG. 3B). One of these compounds, RNPA1000 (FIG. 3C; IC$_{50}$=100-125 µM), did not affect the activity of the commercially available E. coli RNase HI, RNase A, RNase I or in-house purified S. aureus RNase J1 at any concentration tested (0-750 µM), but did mildly inhibit E. coli RNase III activity (IC$_{50}$=500-750 µM; data not shown). These and other data (see below) suggest that RNPA1000 may have specificity for S. aureus RnpA, yet as with any small molecule we cannot rule out the possibility that the agent may also affect other S. aureus enzymes. To assess whether RnpA-inhibitory agents exhibit potential as antimicrobials, a series of experiments were performed to evaluate whether RNPA1000 inhibited S. aureus growth and could limit S. aureus pathogenesis in a systemic model of infection.

Example 4

Antimicrobial Susceptibility Testing

With the exception of RN4220-derivatives, in vitro activities of RNPA1000 against bacteria were determined by the broth microdilution method according to the Clinical and Laboratory Standards Institute (CLSI) guidelines using cation adjusted Mueller-Hinton broth or MH broth supplemented with 5% lysed horse blood (for testing Streptococcus spp.). Microtiter plates containing serial dilutions of RNPA1000 (0, 4, 8, 16, 32, 64, and 128 µg/ml) were inoculated with $10^5$ colony forming units (CFU)/ml and incubated for 18 hr at 37° C. The MIC for each isolate was defined as the lowest concentration of RNPA1000 that completely inhibited growth of the organism as detected by the unaided eye. The MIC for each S. aureus strain was further refined by repeat testing following the procedure described above, except that microtiter wells contained 1 µg/ml incremental increases in concentration of RNPA1000 spanning the lowest concentration that initially did not completely inhibit growth (16 µg/ml) and the concentration that completely inhibited growth (32 µg/ml). The MIC value for each S. aureus strain was determined to be the median score of replicate measurements (n=5). Wells containing concentrations of RNPA1000≥MIC were plated for minimal bactericidal measurement. Where possible, experiments with VRSA strains were performed in a laminar flow hood to minimize potential for equipment contamination. For RN4220 cells containing plasmid vector (pCN51), RnpA overproducing plasmid (pRNPA-S) or RnpA underproducing plasmid (pRNPA-A.S.) in vitro antimicrobial activity of RNPA1000 was performed by the microdilution method as described above, except that cells were grown in Tryptic Soy Broth medium supplemented with 2.5 µM CdCl$_2$ and 0, 1, 2, 4, 8, 16, 32, 64, or 128 µg/ml RNPA1000. Time-kill assays were also performed to monitor the antimicrobial properties of RNPA1000 for S. aureus strain UAMS-1 in the absence and presence of 0.25, 0.5, 2, and 4 times the strain's MIC for oxacillin (1 µg/ml), rifampicin (0.5 µg/ml), vancomycin (2 µg/ml), or daptomycin (1 µg/ml). The indicated amount of RNPA1000 and/or commercial antibiotic were added to mid-exponential phase ($2 \times 10^8$ cfu/ml) S. aureus strain UAMS-1 cells and incubated at 37° C. Aliquots were removed at 0, 2, 4, 8, and 24 hr post-antimicrobial challenge, serial diluted, and plated to enumerate resulting cfu/ml. All time-kill assays were repeated at least 3 times. Results are provided in Table 1.

TABLE 1

| Organism (Phenotype) | Strain[b] | MIC (μg/ml)[b,c] | Organism (Phenotype) | Strain[b] | MIC (μg/ml)[c,d] |
|---|---|---|---|---|---|
| S. aureus (MRSA) | USA100 | 26 | S. pneumoniae (MDR) | Isolate 4 | 32 |
| S. aureus (MRSA) | USA200 | 32 | S. pneumoniae (MDR) | Isolate 5 | 16 |
| S. aureus (MRSA) | USA300 | 23 | S. pyogenes | Isolate 1 | 8 |
| S. aureus (MRSA) | USA400 | 23 | S. sanguis | Isolate 1 | 16 |
| S. aureus (MRSA) | USA500 | 23 | S. bovis | ATCC49147 | 32 |
| S. aureus (MRSA) | USA600 | 32 | E. faecalis | Isolate 1 | 64 |
| S. aureus (MRSA) | USA700 | 32 | E. faecalis | Isolate 2 | 64 |
| S. aureus (MRSA) | USA800 | 23 | E. faecalis | Isolate 3 | 64 |
| S. aureus (MRSA) | USA900 | 32 | E. faecalis | Isolate 4 | 64 |
| S. aureus (MRSA) | USA1000 | 29 | E. faecalis | Isolate 5 | 64 |
| S. aureus (MRSA) | USA1100 | 32 | E. faecium | Isolate 1 | 64 |
| S. aureus (MSSA) | UAMS-1 | 26 | E. faecium | Isolate 2 | 64 |
| S. aureus (VISA) | VISA-NRS1 | 32 | E. faecium | Isolate 3 | 64 |
| S. aureus (VISA) | VISA-NRS3 | 16 | E. faecium | Isolate 4 | 64 |
| S. aureus (VISA) | Isolate 3 | 16 | E. faecium | Isolate 5 | 64 |
| S. aureus (VISA) | Isolate 4 | 32 | E. faecium | Isolate 5 + reserpine | 32 |
| S. aureus (VISA) | Isolate 5 | 16 | | | |
| S. aureus (VRSA) | VRSA-VRS1 | 16 | E. faecium (VRE) | Isolate 1 | 64 |
| S. aureus (VRSA) | VRSA-VRS10 | 32 | E. faecium (VRE) | Isolate 2 | 64 |
| S. epidermidis | Isolate 1 | 16 | E. faecium (VRE) | Isolate 3 | 32 |
| S. epidermidis | Isolate 2 | 8 | E. faecium (VRE) | Isolate 4 | 64 |
| S. epidermidis | Isolate 3 | 8 | E. faecium (VRE) | Isolate 5 | 32 |
| S. epidermidis | Isolate 4 | 8 | B. cereus | Isolate 1 | 8 |
| S. epidermidis | Isolate 5 | 8 | E. coli | Isolate 1 | >64 |
| S. agalactiae | Isolate 1 | 16 | E. coli | Isolate 2 | >64 |
| S. agalactiae | Isolate 2 | 32 | E. coli | Isolate 3 | >64 |
| S. agalactiae | Isolate 3 | 32 | E. coli | Isolate 4 | >64 |
| S. agalactiae | Isolate 4 | 32 | E. coli | Isolate 5 | >64 |
| S. pneumoniae | Isolate 1 | 16 | A. baumannii | Isolate 1 | >64 |
| S. pneumoniae | Isolate 2 | 16 | A. baumannii | Isolate 2 | >64 |
| S. pneumoniae | Isolate 3 | 16 | A. baumannii | Isolate 3 | >64 |
| S. pneumoniae | Isolate 4 | 32 | A. baumannii | Isolate 4 | >64 |
| S. pneumoniae | Isolate 5 | 16 | A. baumannii | Isolate 5 | >64 |
| S. pneumoniae (MDR) | Isolate 1 | 32 | A. baumannii | Isolate 5 + reserpine | >64 |
| S. pneumoniae (MDR) | Isolate 2 | 32 | | | |
| S. pneumoniae (MDR) | Isolate 3 | 16 | | | |

[a]Organism and relavent antibiotic resistance phenotype provided (in parenttheses); methicillin resistant S. aureus (MRSA); vancomycin intermediate S. aureus (VISA); vancomycin resistant S. aureus (VRSA); multidrug resistant S. pneumoniae (MDR); vancomycin resistant E. faecium (VRE).
[b]With the exception of S. aureus and S. bovis, all strains were clinical blood isolates; USA-types (U.S. MRSA lineages) were obtained from the Centers for Disease Control and Prevention; S. aureus strain UAMS-1 is a clinical osteomyelitis isolate; isolates NRS1, NRS3, VRS1 and VRS10 were obtained through the Network of Animicrobial Resistance in Staphylococcus aureus (NARSA); S. bovis strain ATCC49147 was obtained from the American Type Culture Collection.
[c]Each S. aureus isolate was tested 5 times; other organisms were tested in duplicate.
[d]Minimum inhibitory concentration (MIC) was determined following the Clinical and Laboratory Standards Institute (CLSI) guidelines for antimicrobial susceptibility testing. S. aureus MRSA isolates were subsequently more accurately measured.

Figure 7:
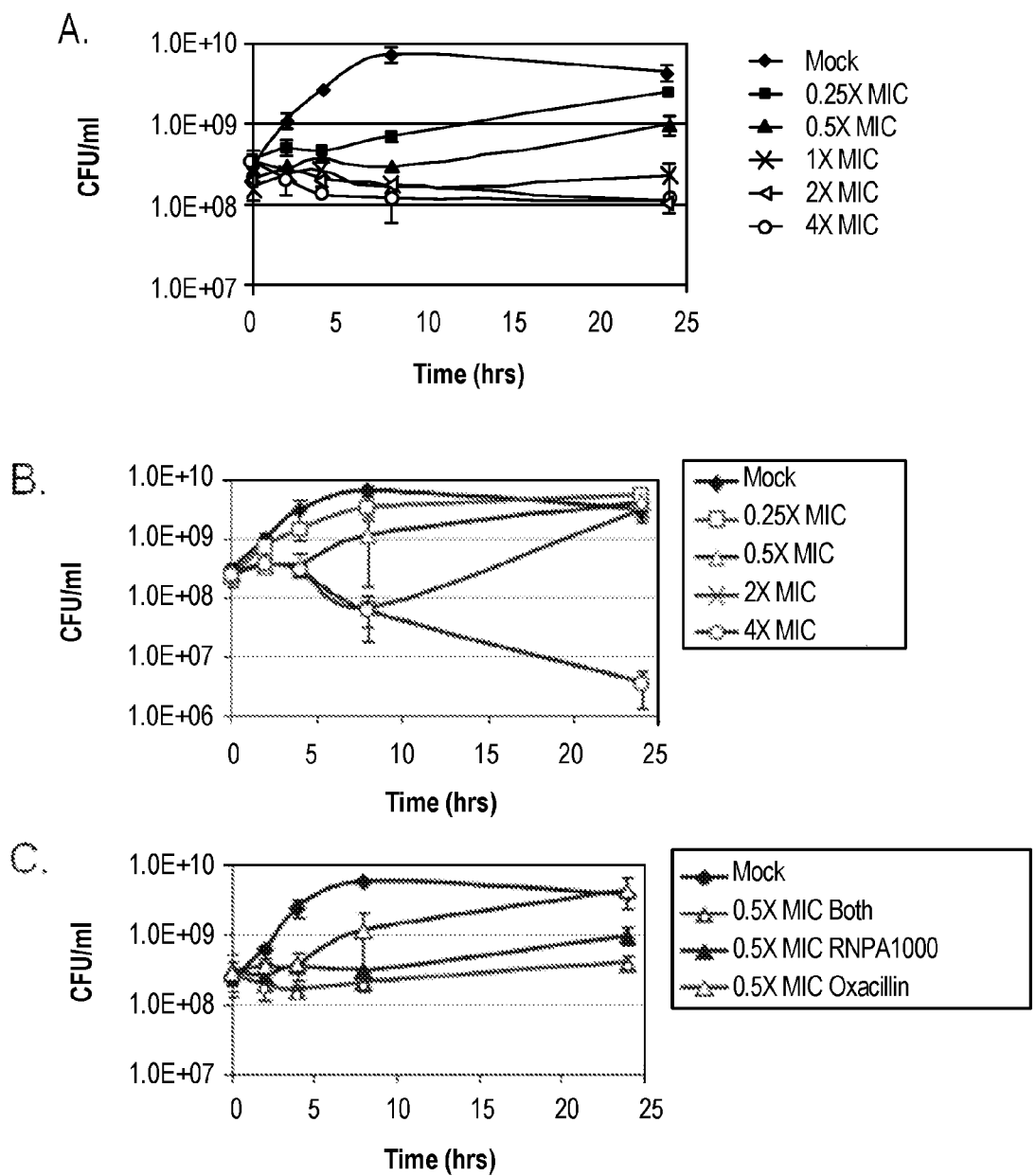
FIG. 7 shows the *S. aureus* time-kill assay results. Panel A depicts the mid-exponential phase for *S. aureus* strain UAMS-1 cells that were treated with 0.25, 0.5, 1, 2, or 4 times the MIC for RNPA1000. Plotted are the average cfu/ml at 0, 2, 4, 8, and 24 hr post-RNPA1000 addition for each drug concentration tested (n=3); standard deviation shown. Panel B shows the average cfu/ml at 2, 4, 8, and 24 hr post-oxacillin treatment (0.25, 0.5, 2, or 4 times the MIC; n=3) of mid-exponential phase cells. Panel C shows the mid-exponential phase cells were treated with 0.5 times the MIC for RNPA1000, oxacillin, or both (RNPA1000 and oxacillin). Shown are the average cfu/ml of mid exponential phase cells following 2, 4, 8, and 24 hr post treatment (n=3); standard deviation shown.
Figure 8:
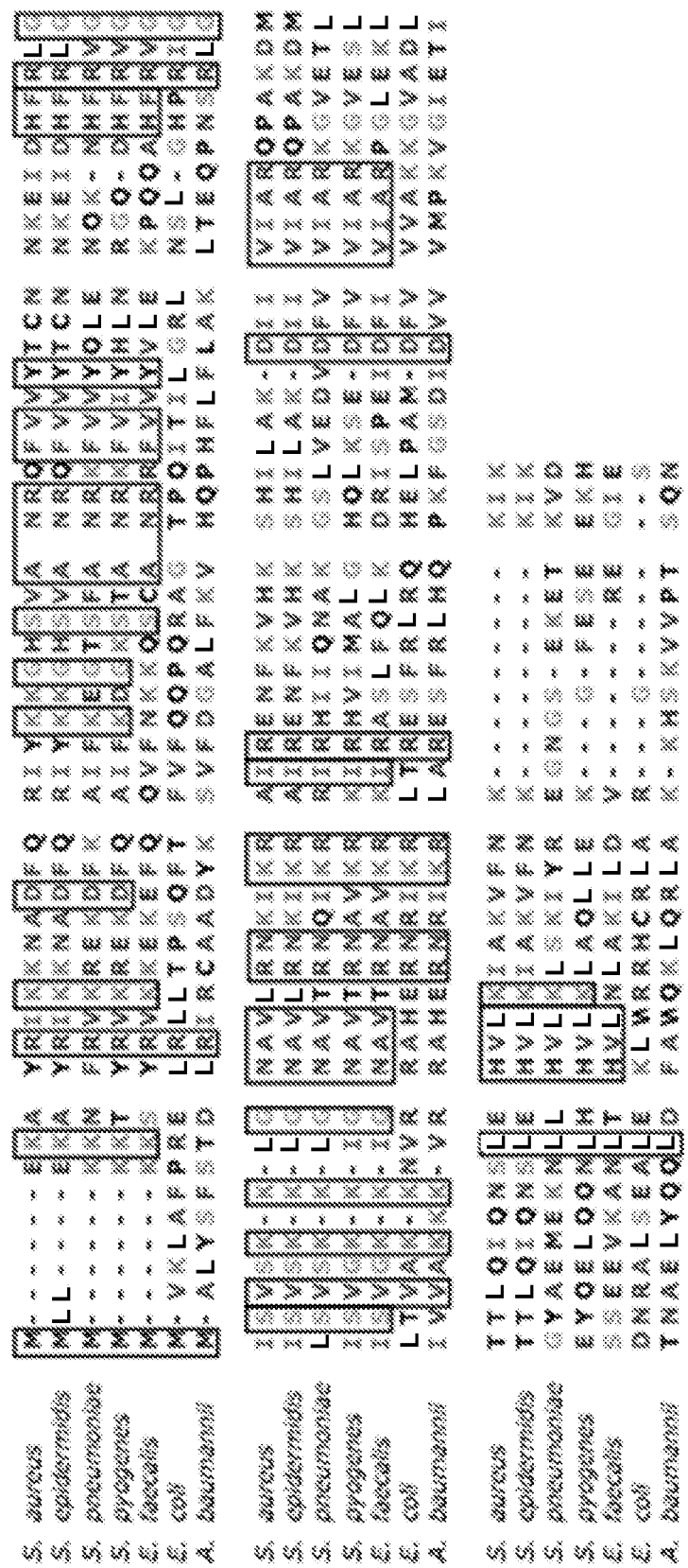
FIG. 8 is a table showing the alignment of amino acid sequences of RnpA using GramAlign with default parameters. Conserved amino acids are boxed. The sequence for *S. aureus* is SEQ ID NO. 1; for *S. epidermidis* is SEQ ID NO. 2; for *S. pneumonia* is SEQ ID NO. 3; for *S. pyogenes* is SEQ ID NO. 4; for *E. faecalis* is SEQ ID NO. 5; for *E. coli* is SEQ ID NO. 6; and for *A. baumannii* is SEQ ID NO. 7.

As shown in Table 1, RNPA1000 demonstrated moderate antimicrobial activity against two well-characterized genotypically diverse S. aureus isolates, UAMS-1 (clinical osteomyelitis isolate; MIC 26 μg/ml) and USA300-0114 [predominant cause of U.S. community-associated methicillin resistant S. aureus infections (MRSA); MIC 23 μg/ml], as well as representatives of other major MRSA lineages circulating throughout the US (see McDougal et al., J Clin Microbial, 41: 5113-5120 (2003)). Likewise, RNPA1000 demonstrated antimicrobial activity against vancomycin-intermediate susceptible S. aureus (VISA) and vancomycin resistant S. aureus (VRSA). Time kill assays revealed that RNPA1000 acts as a bacteriostatic agent (FIG. 7, Panel A), and that it does not affect the antimicrobial activities of other anti-staphylococcal agents, including vancomycin, daptomycin, or rifampicin (data not shown), but does mildly increase the potency of oxacillin (FIG. 7, Panels B and C). The RnpA-inhibitor also exhibited antimicrobial activity against Staphylococcus epidermidis, antibiotic susceptible and multi-drug resistant Streptococcus pneumoniae, Streptococcus pyogenes, Streptococcus agalactiae, and Bacillus cereus. RNPA1000 also showed mild activity against Enterococcus faecalis, Enterococcus faecium and vancomycin resistant E. faecium (VRE), but did not affect Escherichia coli or Acinetobacter baumannii growth (Table 1). The latter was expected because E. coli and A. baumannii RnpA share limited amino acid identity (24% and 26%, respectively) with S. aureus RnpA (FIG. 8). Moreover, purified A. baumannii RnpA did not demonstrate ribonuclolytic activity in our assay conditions (data not shown). Enterococci susceptibility to RNPA1000 was increased from an MIC of 64 μg/ml to 32 μg/ml in the presence of the efflux pump inhibitor reserpine, suggesting that enterococci may be inherently susceptible to the RnpA inhibitor. Conversely, the efflux inhibitor had no effect on A. baumannii RNPA1000 susceptibility (Table 1). Taken together, these results indicate that bacterial RNPA1000 susceptibility correlates with amino acid similarity to S. aureus RnpA and the enzyme's RNA degradation activity.

To assess whether the susceptibility of S. aureus to RNPA1000 was attributable to the inhibition of cellular RnpA, the mRNA turnover properties of S. aureus that were challenged with a sub-inhibitory concentration of RnpA-inhibitor (0.5×MIC) were directly measured. Following 30 min treatment, RNPA1000 reduced the mRNA degradation rate of S. aureus cells, in comparison to mock treated cells (FIG. 5A). Thus, RnpA-inhibitory compounds reduce cellular mRNA degradation, presumably by limiting the enzyme's cellular function. The mRNA turnover properties of RNPA1000 treated cells resembled that of RnpA depleted cells (FIG. 2E), suggesting that the agent may be affecting the enzyme. To more directly determine whether RNPA1000's antimicrobial effects are mediated through cellular inhibition of RnpA, the RNPA1000 susceptibility of *S. aureus* RnpA over- and under-producing cells was assessed. *S. aureus* harboring vector, or a plasmid copy of wild type rnpA mRNA or rnpA antisense RNA under control of the $CdCl_2$ inducible promoter were grown in the presence of 2.5 μM inducer and increasing concentrations of RNPA1000. As stated above, this concentration of cadmium chloride induces mild changes in RnpA protein expression (RnpA overproduction or underproduction) but is modest enough that cellular growth is not affected. As shown in FIG. 5B, both vector containing- and RnpA overproducing-cells exhibited an MIC of 32 μg $ml^{-1}$, whereas the MIC of RnpA underproducing cells was 8 μg $ml^{-1}$. The latter indicates that *S. aureus*' RNPA1000 susceptibility correlates to cellular RnpA levels and that the agent's antimicrobial mode-of-action is, in part, RnpA dependent.

Example 5

Cytotoxicity Assays

It was then assessed whether RnpA-inhibitory agent concentrations corresponding to the effective bacterial MIC values (10-50 μg/ml) elicited human cell cytotoxicity. HepG2 human hepatocytes ($10^5$ cells) were seeded in individual wells of a microtitre plate and incubated for 16 hr at 37° C. with 5% carbon dioxide in Dulbecco's Modified Eagle Media supplemented with 10% fetal bovine serum. Cells were then challenged with Mitomycin C (5 μg/ml; positive control) or 0, 25, or 50 μg/ml RNPA1000 for either 24 or 48 hrs. Cell viability was measured spectrophotometrically (570 nm) following the addition and subsequent reduction of tetrazolium salt (MTT) within metabolically active cells, as per the manufacturer's recommendations (American Type Culture Collection; Manassas, Va.).

MTT cell proliferation assay measurements revealed that 24 hr RnpA-inhibitor exposure did not cause human HepG2 cell toxicity at any concentration tested (data not shown). However, extended RNP1000 exposure (48 hr) elicited mild cytotoxicity at 25 μg/ml, which corresponds to the minimum inhibitory concentration of most MRSA lineages (FIG. 4A), whereas higher concentrations exhibited increased toxicity (data not shown).

Example 6

Antimicrobial Efficacy of RnpA-inhibitor on Biofilm-associated Bacteria

The success of *S. aureus* as a bacterial pathogen can be attributable, in part, to its ability to form biofilms on implanted medical devices, which presumably provides a focus for bacterial dissemination to secondary host sites. One of the complicating issues in treating biofilm-associated infections is that biofilm-associated bacteria are inherently recalcitrant to antibiotic treatment. For instance, one recent in vitro study showed that despite using a strain that was intrinsically susceptible to each antibiotic, 5×MIC of daptomycin, linezolid, or vancomycin only reduced biofilm-associated bacteria by <2 logs following 24 hr treatment and none of these antibiotics cleared biofilm-associated *S. aureus* even when administered at 20×MIC over a course of 3 days (see Weiss et al., *Antimicrob Agents Chemother*, 53: 2475-2482 (2009)). Transcription profiling studies have revealed that despite being physiologically unique, biofilm-associated *S. aureus* resemble planktonic stationary phase cells (see Beenken et al., *J Bacteriol*, 186: 4665-4684 (2004)). Indeed, similar to stationary phase bacteria, rnpA expression is diminished 4.3 and 6.2-fold in *S. aureus* biofilm-associated and biofilm-detached bacteria, respectively, in comparison to exponential phase cells (Dunman and Horswill, unpublished). Because low levels of RnpA are likely to be present within biofilm-associated bacteria, fewer RnpA-inhibitory molecules could be required to interfere with the protein's function and, consequently, antimicrobial activity. Thus, biofilm-associated *S. aureus* may exhibit considerable susceptibility to an RnpA-inhibitor, such as RNPA1000.

To determine this, in vitro biofilm assays were performed as described in Weiss et al., *Antimicrob Agents Chemother*, 53: 2475-2482 (2009). Briefly, 1 cm segments of 14-gauge fluorinated ethylene propylene Introcan Safety Catheters (B. Braun, Bethlehem, Pa.) were coated with human plasma and placed in individual wells of a 12-well microtiter plate containing 2 ml biofilm medium and *S. aureus* strain UAMS-1 at a final $OD_{600\ nm}$ of 0.05. Following overnight incubation at 37° C. catheters were removed, rinsed in phosphate buffered saline (PBS), and transferred to fresh biofilm medium containing 0, 5, 10, or 20 times the *S. aureus* MIC for RNPA1000. Catheters exposed to each dose (n=3) were recovered daily over a period of 3 days, with the medium being replaced each day. After each recovery time point catheters were rinsed in PBS and adherent bacteria were enumerated by sonication and plating. Analysis of variance (ANOVA) of logarithmically-transformed bacterial count data was used to evaluate the effect of RNPA1000 exposure.

Figure 4:
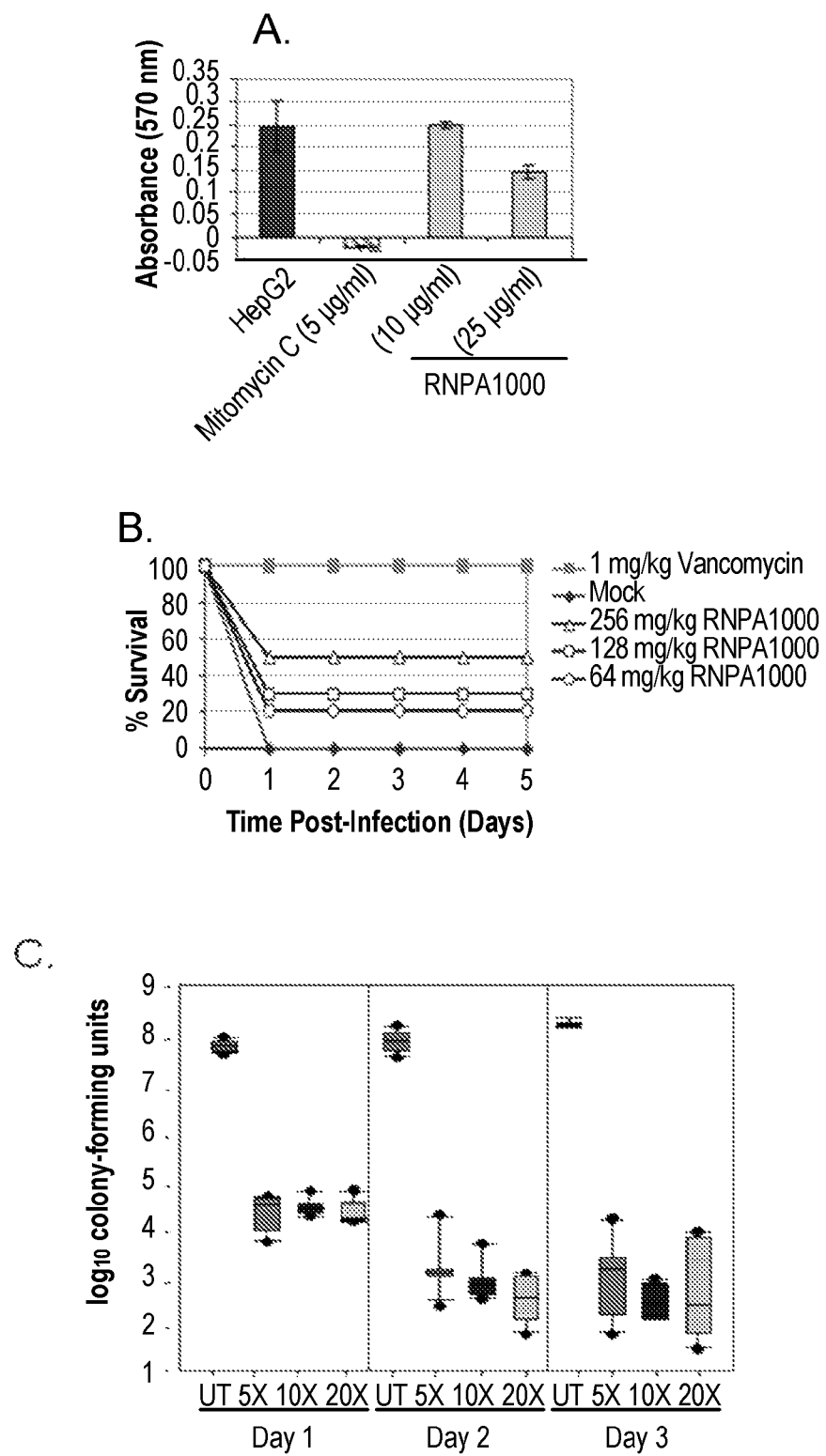
FIG. 4, Panel A shows the MTT-cytotoxicity assay results of HepG2 cells exposed to compound solvent (DMSO; negative control), Mitomycin C (positive control), and indicated amount of RNPA1000. Panel B shows the average daily (X-axis) percent surviving animals (Y-axis) following no treatment (closed diamonds; negative control), vancomycin treatment (closed squares; 1 mg/kg; positive control), or RNPA1000 treatment; 64 mg/kg (open circles); 128 mg/kg (open squares), 256 mg/kg (open triangles). Panel C shows the number of catheter-associated *S. aureus* following 1, 2, or 3 days of no antimicrobial treatment (untreated; UT) or exposure to 5, 10, or 20 times the MIC for RNPA1000. Boxes define the interval between the $25^{th}$ and $75^{th}$ percentile. Bars extending upward indicate the boundary defined by the value 1.5× higher than the $75^{th}$ percentile while those extending downward indicate the boundary defined by a value 1.5× lower than the $25^{th}$ percentile. Filled circles indicate individual values outside these two extremes.

As shown in FIG. 4C, treatment of biofilm-associated *S. aureus* with 5×MIC RNPA1000 for 24 hr resulted in a 3-log decrease in bacterial burden, suggesting that during short term exposure the agent is equally, if not more potent, than daptomycin, vancomycin, or linezolid. Further, while bacterial clearance was never achieved, increasing the length of exposure or RNPA1000 concentration enhanced antimicrobial activity. Maximal RNPA1000 antimicrobial potency (5-log reduction in biofilm-associated bacteria) compared favorably with the activities of commercially available antibiotics assessed in the same model and conditions (6-log decrease daptomycin, 5-log decrease linezolid; 4-log decrease vancomycin) (see Weiss et al., *Antimicrob Agents Chemother*, 53: 2475-2482 (2009)). Taken together, these results suggest that RnpA plays an important biological role in *S. aureus* biofilm maintenance, and that corresponding inhibitors may have expanded therapeutic utility in treating biofilm-associated infections.

Example 7

Acute Lethal Model of Infection

Because RNPA1000 was not toxic during short- and only mildly toxic during extended-HepG2 exposure, it could serve as an appropriate tool to assess whether RnpA-inhibitory molecules are efficacious in a systemic mouse infection model. Female 5-6 week old CD-1 mice were challenged by intraperitoneal injection (0.5 ml) of wild type *S. aureus* strain Smith, resulting in a final inoculum of $4.55 \times 10^5$ colony forming units/animal; equivalent to 10-100 $LD_{50}s$ and resulted in death of non-treated control animals (N=5) within 24 hr post-inoculum. RNPA1000 was solubilized in 1:1 mixture of DMSO and PEG400; Vancomycin was prepared in water. Animals (5/dose group) were administered 16, 64, and 256 mg/kg or 0.25, 1, 4, and 16 mg/kg of RNPA1000 or Vancomycin, respectively, at 30 min post infection by subcutaneous injection (0.2 ml). The percent surviving animals receiving no treatment, a single dose of Vancomycin, or RnpA-inhibitor was recorded daily over the course of the study (5 days). The results are shown in Table 2 and FIG. 4B.

TABLE 2

| Dose (mg/kg) | % Survival | | |
|---|---|---|---|
| | RNPA1000 | Vancomycin | RNPA1000 (alone) |
| 0 | 0 | 0 | 100(2) |
| 0.25 | — | 0 | — |
| 1 | — | 100 | — |
| 4 | — | 100 | — |
| 16 | 20; 20(2) | 100 | 100(2) |
| 64 | 40; 20(2) | — | 100(2) |
| 256 | 60; 40; 60(3) | — | 100(2) |

Percent survival refers to a consensus of surviving animals following 5 days post-intraperitoneal *S. aureus* injection and RNPA1000 administration. The number in parentheses indicates the number of times the experiment was repeated. Each member of non-treated control mice expired within 24 hr bacterial inoculation (0 mg/kg). Vancomycin served as a positive control.

As shown in FIG. 4B, subcutaneous injection of RNPA1000 limited the lethal effects of wild type *S. aureus* injected ($4.55 \times 10^5$ cfu/animal) into the intraperitoneal cavity of CD-1 mice. Although this bacterial inoculum (equivalent to 10-100 $LD_{50}s$) resulted in 100% death of non-treated control animals within 24 hr, RNPA1000 provided protection in a dose-dependent manner. Administration of the highest RnpA-inhibitor dose (256 mg/kg) reproducibly resulted in 50% survival, whereas 128 mg/kg and 64 mg/kg resulted in 30% and 20% survival, respectively, over the course of study (FIG. 4B; Table 2). Notably, dosing regimens of compound (alone) did not affect animal survival at any of the concentrations tested (32 mg/kg, 64 mg/kg, 128 mg/kg, 256 mg/kg; Table 2). Taken together, these results suggest that RNPA1000 limits bacterial pathogenicity within the acute lethal model of *S. aureus* infection with a median effective dose ($ED_{50}$) between 64-256 mg/kg. Thus, RNPA1000 could be considered a platform for medicinal chemistry-based generation of more potent derivatives. These results also provide proof of concept that RnpA inhibitory agents are efficacious in a systemic mouse infection model and that RNPA1000 represents a tool to study the contribution of RnpA to infection processes.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A method of treating a Gram positive bacterial infection in a subject, comprising administering to the subject:
an effective amount of an RNase inhibitor of the following structure:

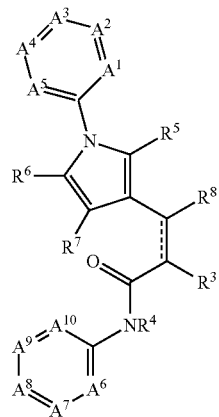

or a pharmaceutically acceptable salt or prodrug thereof; and an antibacterial compound.

2. The method of claim 1, wherein the bacterial infection is a *Staphylococcus* infection.

3. The method of claim 1, wherein the bacterial infection is a *Staphylococcus aureus* infection.

4. The method of claim 3, wherein the *Staphylococcus aureus* infection is a drug-resistant *Staphylococcus aureus* infection.

5. The method of claim 3, wherein the *Staphylococcus aureus* infection is a biofilm-associated *Staphylococcus aureus* infection.

6. The method of claim 1, wherein the RNase inhibitor is an RnpA inhibitor.

7. The method of claim 1, wherein the antibacterial compound is selected from the group consisting of astromicin, biapenem, ciprofloxacin, clinafloxacin, clindamycin, daptomycin, dihydrostreptomycin, enoxacin, fleroxacin, gentamicin, imipenem, kanamycin, linezolid, lomefloxacin, meropenem, neomycin, norfloxacin, ofloxacin, pefloxacin, piperacillin, quinupristin, sparfloxacin, spectinomycin, streptomycin, sulopenem, temafloxacin, ticarcillin, tobramycin, tosufloxacin, vancomycin, and virginiamycin.

* * * * *